US010806356B2

(12) United States Patent
Lee et al.

(10) Patent No.: US 10,806,356 B2
(45) Date of Patent: Oct. 20, 2020

(54) ELECTRONIC DEVICE AND METHOD FOR MEASURING HEART RATE BASED ON INFRARED RAYS SENSOR USING THE SAME

(71) Applicant: Samsung Electronics Co., Ltd., Suwon-si, Gyeonggi-do (KR)

(72) Inventors: Donghyun Lee, Yongin-si (KR); Dongwook Kim, Seoul (KR); Jinhee Won, Ansan-si (KR); Jaesung Lee, Seongnam-si (KR); Jongmin Choi, Seoul (KR); Taeho Kim, Cheongju-si (KR); Jeongmin Park, Hwaseong-si (KR); Seungeun Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 553 days.

(21) Appl. No.: 15/682,971

(22) Filed: Aug. 22, 2017

(65) Prior Publication Data

US 2018/0055392 A1 Mar. 1, 2018

(30) Foreign Application Priority Data

Aug. 26, 2016 (KR) ........................ 10-2016-0109101

(51) Int. Cl.
*A61B 5/024* (2006.01)
*G06F 21/32* (2013.01)
(Continued)

(52) U.S. Cl.
CPC ........ *A61B 5/02433* (2013.01); *A61B 5/0077* (2013.01); *A61B 5/024* (2013.01);
(Continued)

(58) Field of Classification Search
CPC ... A61B 5/02433; A61B 5/0077; A61B 5/024; A61B 2576/00; G06F 21/32; G06K 9/00906; G06T 7/0012
See application file for complete search history.

(56) References Cited

U.S. PATENT DOCUMENTS

| | | | | |
|---|---|---|---|---|
| 6,594,377 | B1 | 7/2003 | Kim et al. | |
| 9,750,420 | B1 * | 9/2017 | Agrawal | A61B 5/02427 |

(Continued)

FOREIGN PATENT DOCUMENTS

| | | | |
|---|---|---|---|
| JP | 2007-534421 | A | 11/2007 |
| JP | 2011-130996 | A | 7/2011 |

(Continued)

OTHER PUBLICATIONS

International Search Report dated Nov. 17, 2017, issued in International Application No. PCT/KR2017/009203 filed on Aug. 23, 2017.

(Continued)

*Primary Examiner* — Santiago Garcia
(74) *Attorney, Agent, or Firm* — Jefferson IP Law, LLP

(57) ABSTRACT

A method for determining a heart rate (HR) using an infrared rays (IR) sensor and an electronic device is provided. An image is received using an IR sensor, at least one region of interest (ROI) for measuring the HR is determined in the received image, and the HR is determined based on the at least one determined ROI.

15 Claims, 16 Drawing Sheets

(51) Int. Cl.
*G06T 7/00* (2017.01)
*A61B 5/00* (2006.01)
*G06K 9/00* (2006.01)

(52) U.S. Cl.
CPC ......... *G06F 21/32* (2013.01); *G06K 9/00906* (2013.01); *G06T 7/0012* (2013.01); *A61B 2576/00* (2013.01)

(56) References Cited

U.S. PATENT DOCUMENTS

| | | | |
|---|---|---|---|
| 10,004,411 | B2 * | 6/2018 | Chen ..................... G06T 7/0016 |
| 2008/0234590 | A1 | 9/2008 | Akkermans et al. |
| 2014/0303454 | A1 | 10/2014 | Clifton et al. |
| 2014/0336478 | A1 | 11/2014 | Segman |
| 2015/0038810 | A1 | 2/2015 | Melker |
| 2015/0148687 | A1 | 5/2015 | Kitajima et al. |
| 2016/0106329 | A1 * | 4/2016 | Hoof .................... A61B 5/0261 600/479 |
| 2016/0132732 | A1 | 5/2016 | Gunther et al. |
| 2016/0191822 | A1 | 6/2016 | Kosugou |
| 2016/0342782 | A1 * | 11/2016 | Mullins ................... G06F 21/32 |
| 2016/0360970 | A1 * | 12/2016 | Tzvieli ................. A61B 5/6803 |
| 2017/0063549 | A1 | 3/2017 | Zwart et al. |
| 2018/0042486 | A1 * | 2/2018 | Yoshizawa ......... A61B 5/02416 |
| 2018/0092588 | A1 * | 4/2018 | Tzvieli ................. H04N 5/2257 |
| 2018/0116528 | A1 * | 5/2018 | Tzvieli ................... A61B 5/163 |
| 2018/0153455 | A1 * | 6/2018 | Guazzi ................. A61B 5/0077 |

FOREIGN PATENT DOCUMENTS

| | | | |
|---|---|---|---|
| JP | 2013-064645 | A | 4/2013 |
| JP | 2015-177403 | A | 10/2015 |
| KR | 10-2012-0035964 | A | 4/2012 |
| KR | 10-2014-0057868 | A | 5/2014 |
| KR | 10-2014-0058573 | A | 5/2014 |
| WO | 2015-124770 | A1 | 8/2015 |

OTHER PUBLICATIONS

European Search Report dated Dec. 22, 2017, issued in European Application No. 17187715.2.

* cited by examiner

ESTIMATED HEART RATE: 0.9333*60 = 55.98bpm

ESTIMATED HEART RATE: 1.000×60 = 60.00bpm

ESTIMATED HEART RATE: 0.9667·60 = 58.002bpm

ESTIMATED HEART RATE: 1.167·60 = 70.02bpm

ELECTRONIC DEVICE AND METHOD FOR MEASURING HEART RATE BASED ON INFRARED RAYS SENSOR USING THE SAME

CROSS-REFERENCE TO RELATED APPLICATION(S)

This application claims the benefit under 35 U.S.C. § 119(a) of a Korean patent application filed on Aug. 26, 2016 in the Korean Intellectual Property Office and assigned Serial number 10-2016-0109101, the entire disclosure of which is hereby incorporated by reference.

TECHNICAL FIELD

The present disclosure relates to a method for measuring a heart rate (HR) based on an infrared rays (IR) sensor and an electronic device.

BACKGROUND

With the widespread of portable electronic devices and the development of technology, users can utilize portable electronic devices in various ways. For example, portable electronic devices may be used as measurement means for measuring health information of users, and may also be used as authentication means for authenticating users. Users may measure their own heart beats per minute (hereinafter referred to as “heart rate (HR)”) using sensors that are built in the portable electronic devices to measure their HRs. In general, a portable electronic device may measure the HR of a user through a part of the user’s body that comes in contact with the portable electronic device for measurement of the HR. The portable electronic device may determine the HR of the user based on the measured HR information. Further, the portable electronic device may be used as an authentication means for authenticating the user based on user’s inherent information that is set by the user, such as fingerprint information, iris information, password, or pattern information.

The above information is presented as background information only to assist with an understanding of the present disclosure. No determination has been made, and no assertion is made, as to whether any of the above might be applicable as prior art with regard to the present disclosure.

SUMMARY

In general, in the case of utilizing a portable electronic device as a means for measuring a heart rate (HR), it is necessary for a user to intentionally come in contact with a HR sensor of the portable electronic device. On the other hand, a camera may be used to detect a change of a user’s skin color and to measure the HR based on the detected change of the skin color. However, if the surroundings are darkened, the change of the skin color may be unable to be detected, and thus it may be difficult to measure the HR.

Aspects of the present disclosure are to address at least the above-mentioned problems and/or disadvantages and to provide at least the advantages described below. Accordingly, an aspect of the present disclosure is to provide an electronic device that can search for a region of interest (ROI) for measuring a HR utilizing an infrared rays (IR) sensor, and measure the HR of a user based on a change of an image in the searched ROI.

In an aspect of the present disclosure, it is possible to measure the HR using an IR sensor in a state where a part of the user’s body does not come in contact with the electronic device, and it is possible to measure the HR regardless of the skin color of the user. In an aspect of the present disclosure, it is also possible to determine iris information of the user using the IR sensor. Another aspect of the present disclosure provides a method for measuring a HR of a user using an IR sensor and a method for authenticating a user.

In accordance with an aspect of the present disclosure, an electronic device is provided. Then electronic device includes an IR sensor, a memory, and a processor electrically connected to the IR sensor and the memory, wherein the memory stores instructions which, when executed, cause the processor to receive an image using the IR sensor, to determine at least one ROI for measuring a HR in the received image, and to determine the HR based on the at least one determined ROI.

In accordance with another aspect of the present disclosure, a method for determining a HR using an IR sensor is provided. The method includes receiving an image using the IR sensor, determining at least one ROI for measuring the HR in the received image, and determining the HR based on the at least one determined ROI.

According to the present disclosure, the HR can be measured using the IR sensor, and the user can be authenticated through sensing the bio information of the user. Accordingly, the security for the electronic device according to the present disclosure can be further strengthened.

According to the present disclosure, since the IR sensor is used, the user’s HR can be measured and the user authentication can be performed without any physical contact with the user even if the surroundings are darkened.

According to the present disclosure, information on the measured HR may be transmitted to another program or device, and it may be utilized by the program or device.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
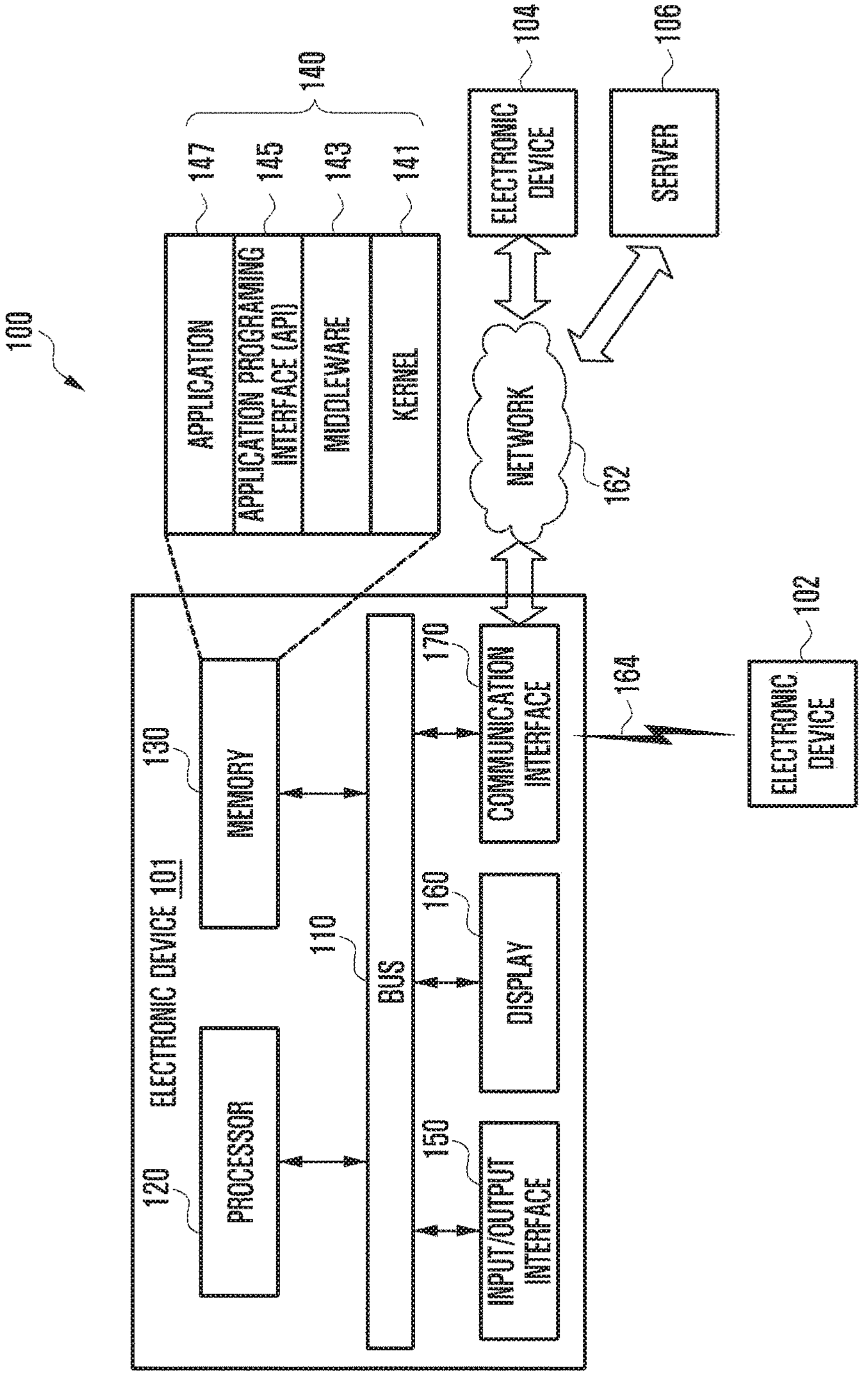
FIG. 1 is a diagram illustrating an electronic device in a network environment according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms “a,” “an,” and “the” include plural referents unless the context clearly dictates otherwise. Thus, for example, reference to “a component surface” includes reference to one or more of such surfaces.

Hereinafter, the present disclosure is described with reference to the accompanying drawings. Although specific embodiments are illustrated in the drawings and related detailed descriptions are discussed in the present specification, the present disclosure may have various modifications and several embodiments. However, various embodiments of the present disclosure are not limited to a specific implementation form and it should be understood that the present disclosure includes all changes and/or equivalents and substitutes included in the spirit and scope of various embodiments of the present disclosure. In connection with descriptions of the drawings, similar components are designated by the same reference numeral.

In various embodiments of the present disclosure, the terms such as “include”, “have”, “may include” or “may have” may be construed to denote a certain characteristic, number, operation, constituent element, component or a combination thereof, but may not be construed to exclude the existence of or a possibility of addition of one or more other characteristics, numbers, operations, constituent elements, components or combinations thereof.

In various embodiments of the present disclosure, the expression “or” or “at least one of A or/and B” includes any or all of combinations of words listed together. For example, the expression “A or B” or “at least A or/and B” may include A, may include B, or may include both A and B.

The expression “1”, “2”, “first”, or “second” used in various embodiments of the present disclosure may modify various components of the various embodiments but does not limit the corresponding components. For example, the above expressions do not limit the sequence and/or importance of the components. The expressions may be used for distinguishing one component from other components. For example, a first user device and a second user device indicate different user devices although both of them are user devices. For example, without departing from the scope of the present disclosure, a first structural element may be referred to as a second structural element. Similarly, the second structural element also may be referred to as the first structural element.

When it is stated that a component is “(operatively or communicatively) coupled to” or “connected to” another component, the component may be directly coupled or connected to another component or a new component may exist between the component and another component. In contrast, when it is stated that a component is “directly coupled to” or “directly connected to” another component, a new component does not exist between the component and another component. In the present disclosure, the expression “configured (or set) to do” may be used to be interchangeable with, for example, “suitable for doing,” “having the capacity to do,” “designed to do,” “adapted to do,” “made to do,” or “capable of doing.” The expression “configured (or set) to do” may not be used to refer to only something in hardware for which it is “specifically designed to do.” Instead, the expression “a device configured to do” may indicate that the device is “capable of doing” something with other devices or parts. For example, the expression “a processor configured (or set) to do A, B and C” may refer to a dedicated processor (e.g., an embedded processor) or a generic-purpose processor (e.g., central processing unit (CPU) or application processor (AP)) that may execute one or more software programs stored in a memory device to perform corresponding functions.

An electronic device according to various embodiments of the present disclosure may be a device including an antenna. For example, the electronic device may be one or more of the following: a smart phone, a tablet personal computer (PC), a mobile phone, a video phone, an e-book reader, a desktop PC, a laptop PC, a netbook computer, a personal digital assistant (PDA), portable multimedia player (PMP), Moving Picture Experts Group (MPEG-1 or MPEG-2) audio layer-3 (MP3) player, a mobile medical application, a camera, and a wearable device (for example, a head-mounted-device (HMD), such as electronic glasses, electronic clothes, an electronic bracelet, an electronic necklace, an electronic appcessary, an electronic tattoo, and a smart watch).

According to some embodiments, the electronic device may be a smart home appliance having an antenna. The smart home appliance may include at least one of the following: a television (TV), a digital versatile disc (DVD) player, an audio player, an air conditioner, a cleaner, an oven, a microwave oven, a washing machine, an air purifier, a set-top box, a TV box (for example, Samsung Home- Sync™, Apple TV™, or Google TV™), game consoles, an electronic dictionary, an electronic key, a camcorder, and an electronic frame.

According to some embodiments, the electronic device may include at least one of the following: various types of medical devices (for example, magnetic resonance angiography (MRA), magnetic resonance imaging (MRI), computed tomography (CT), a scanner, an ultrasonic device and the like), a navigation device, a global positioning system (GPS) receiver, an event data recorder (EDR), a flight data recorder (FDR), a vehicle infotainment device, electronic equipment for a ship (for example, a navigation device for ship, a gyro compass and the like), avionics, a security device, a head unit for a vehicle, an industrial or home robot, an automatic teller machine (ATM) of financial institutions, and a point of sale (POS) device of shops.

According to some embodiments, the electronic device may include at least one of the following: furniture or a part of a building/structure, an electronic board, an electronic signature receiving device, a projector, and various types of measuring devices (for example, a water meter, an electricity meter, a gas meter, a radio wave meter and the like), which are equipped with an antenna. The electronic device according to various embodiments of the present disclosure may also be a combination of the devices listed above. Further, the electronic device according to various embodiments of the present disclosure may be a flexible device. It is apparent to those skilled in the art that the electronic device according to various embodiments of the present disclosure is not limited to the above described devices.

Hereinafter, an electronic device according to various embodiments will be discussed with reference to the accompanying drawings. The term "user" used herein may refer to a human using an electronic device, or may refer to a device (e.g., an artificial intelligence electronic device) using an electronic device.

FIG. 1 illustrates a network environment 100 including an electronic device 101 according to an embodiment of the present disclosure.

Referring to FIG. 1, the electronic device 101, 102, 104 may connect to the server 106 via the network 162 or short-range wireless communication 164. The electronic device 101 may include a bus 110, a processor 120, a memory 130, an input/output interface 150, a display 160, and a communication interface 170. According to some embodiments, at least one of the above described components may be omitted from the electronic device 101 or another component may be further included in the electronic device 101.

The bus 110 may be a circuit connecting the above described components 120, 130, and 150~170 and transmitting communications (e.g., control messages and/or data) between the above described components.

The processor 120 is capable of including one or more of the following: a CPU, an AP, and a communication processor (CP). The processor 120 is capable of controlling at least one of other components of the electronic device 101 and/or processing data or operations related to communication.

The memory 130 is capable of including volatile memory and/or non-volatile memory. The memory 130 is capable of storing data or commands related to at least one of other components of the electronic device 101. According to an embodiment, the memory 130 is capable of storing software and/or a program module 140. For example, the program module 140 is capable of including a kernel 141, middleware 143, application programming interface (API) 145, application programs (or applications) 147, etc. The kernel 141, middleware 143 or at least part of the API 145 may be called an operating system (OS).

The kernel 141 is capable of controlling or managing system resources (e.g., the bus 110, the processor 120, the memory 130, etc.) used to execute operations or functions of other programs (e.g., the middleware 143, API 145, and application programs 147). The kernel 141 provides an interface capable of allowing the middleware 143, API 145, and application programs 147 to access and control/manage the individual components of the electronic device 101.

The middleware 143 is capable of mediating between the API 145 or application programs 147 and the kernel 141 so that the API 145 or the application programs 147 can communicate with the kernel 141 and exchange data therewith. The middleware 143 is capable of processing one or more task requests received from the application programs 147 according to the priority. For example, the middleware 143 is capable of assigning a priority for use of system resources of the electronic device 101 (e.g., the bus 110, the processor 120, the memory 130, etc.) to at least one of the application programs 147. For example, the middleware 143 processes one or more task requests according to a priority assigned to at least one application program, thereby performing scheduling or load balancing for the task requests.

The API 145 refers to an interface configured to allow the application programs 147 to control functions provided by the kernel 141 or the middleware 143. The API 145 is capable of including at least one interface or function (e.g., instructions) for file control, window control, image process, text control, or the like.

The input/output interface 150 is capable of transferring instructions or data, received from the user or external devices, to one or more components of the electronic device 101. The input/output interface 150 is capable of outputting instructions or data, received from one or more components of the electronic device 101, to the user or external devices.

The display 160 is capable of including a liquid crystal display (LCD), a flexible display, a transparent display, a light emitting diode (LED) display, an organic LED (OLED) display, micro-electro-mechanical systems (MEMS) display, an electronic paper display, etc. The display 160 is capable of displaying various types of content (e.g., texts, images, videos, icons, symbols, etc.). The display 160 may also be implemented with a touch screen. In this case, the display 160 is capable of receiving touches, gestures, proximity inputs or hovering inputs, via a stylus pen, or a user's body.

The communication interface 170 is capable of establishing communication between the electronic device 101 and an external device (e.g., a first external device 102, a second electronic device 104, or a server 106). For example, the communication interface 170 is capable of communicating with an external device (e.g., a second external device 104 or a server 106) connected to the network 162 via wired or wireless communication.

Wireless communication may employ, as cellular communication protocol, at least one of the following: long-term evolution (LTE), LTE advance (LTE-A), code division multiple access (CDMA), wideband CDMA (WCDMA), universal mobile telecommunications system (UMTS), wireless broadband (WiBro), and global system for mobile communication (GSM). According to an embodiment, as exemplified as the short-range wireless communication 164 of FIG. 1, wireless communication may include at least one of wireless fidelity (Wi-Fi), light fidelity (LiFi), Bluetooth (BT), BT low energy (BLE), Zigbee, near field communication (NFC), magnetic secure transmission (MST), radio frequency (RF), and body area network (BAN). Wireless communication may also include short-range wireless communication 164. Short-range wireless communication 164 may include at least one of the following: Wi-Fi, BT, NFC, MST, and global navigation satellite system (GNSS). The GNSS may include at least one of the following: GPS, global navigation satellite system (Glonass), Beidou Navigation Satellite System (hereinafter called 'Beidou"), Galileo, the European global satellite-based navigation system, according to GNSS using areas, bandwidths, etc. In the present disclosure, "GPS" and "GNSS" may be used interchangeably. Wired communication may include at least one of the following: universal serial bus (USB), high definition multimedia interface (HDMI), recommended standard 232 (RS-232), and plain old telephone service (POTS). The network 162 may include at least one of the following: a telecommunications network, e.g., a computer network (e.g., local area network (LAN) or wide area network (WAN)), the Internet, and a telephone network.

The first and second external electronic devices 102 and 104 are each identical to or different from the electronic device 101, in terms of type. According to an embodiment, the server 106 is capable of including a group of one or more servers. According to various embodiments, part or all of the operations executed on the electronic device 101 may be executed on another electronic device or a plurality of other electronic devices (e.g., electronic devices 102 and 104 or a server 106). According to an embodiment, when the electronic device needs to perform a function or service automatically or according to a request, it does not perform the function or service, but is capable of additionally requesting at least part of the function related to the function or service from other electronic device (e.g., electronic devices 102 and 104 or a server 106). The other electronic device (e.g., electronic devices 102 and 104 or a server 106) is capable of executing the requested function or additional functions, and transmitting the result to the electronic device 101. The electronic device 101 processes the received result, or further proceeds with additional processes, to provide the requested function or service. To this end, the electronic device 101 may employ cloud computing, distributed computing, or client-server computing technology.

Figure 2:
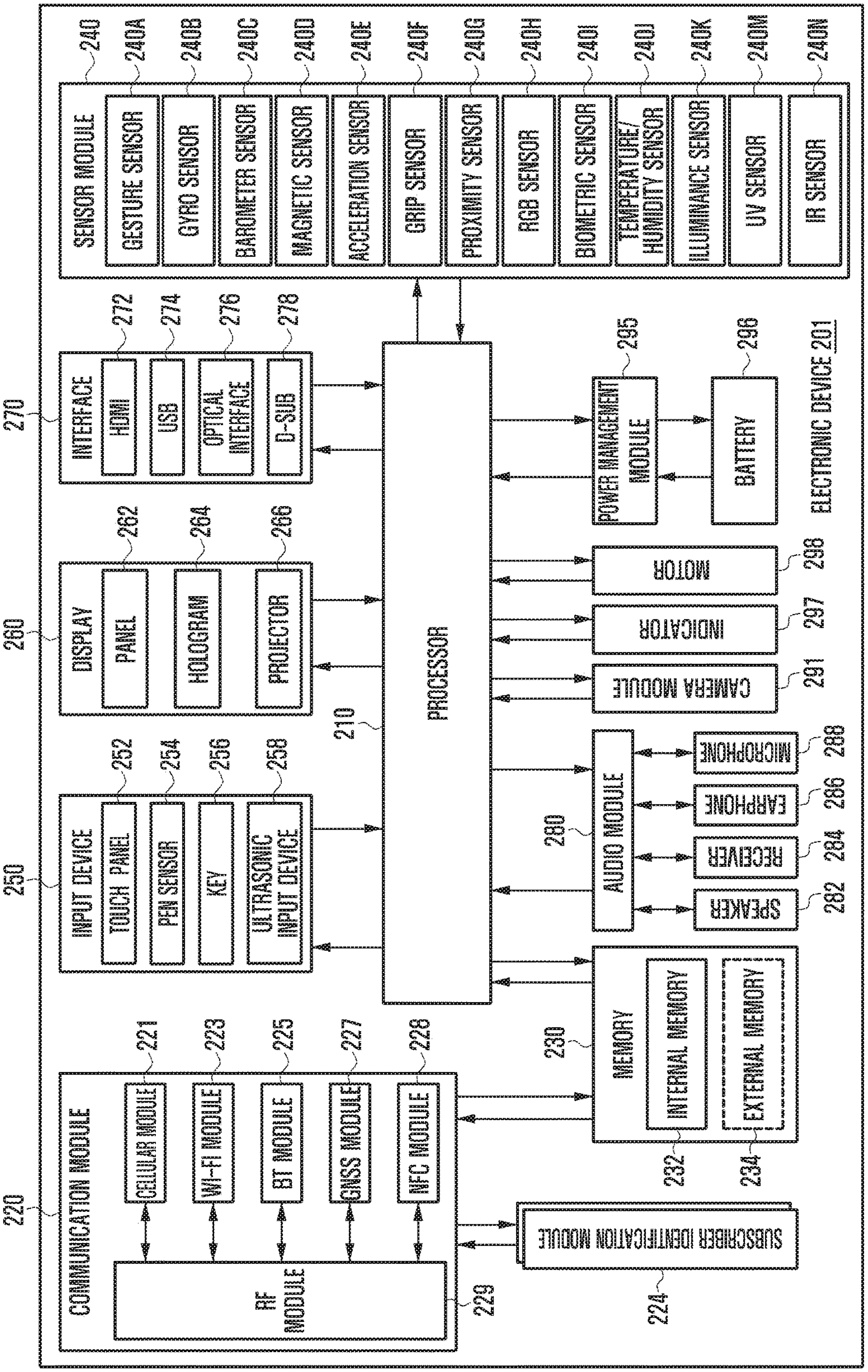
FIG. 2 is a block diagram illustrating the configuration of an electronic device according to an embodiment of the present disclosure.

FIG. 2 is a detailed block diagram showing a configuration of an electronic device 201 according to an embodiment of the present disclosure.

Referring to FIG. 2, the electronic device 201 is capable of including part or all of the components in the electronic device 101 shown in FIG. 1. The electronic device 201 is capable of including one or more processors 210 (e.g., APs), a communication module 220, a subscriber identification module (SIM) 224, a memory 230, a sensor module 240, an input device 250, a display 260, an interface 270, an audio module 280, a camera module 291, a power management module 295, a battery 296, an indicator 297, and a motor 298.

The processor 210 is capable of driving, for example, an operating system or an application program to control a plurality of hardware or software components connected to the processor 210, processing various data, and performing operations. The processor 210 may be implemented as, for example, a system on chip (SoC). According to an embodiment, the processor 210 may further include a graphic processing unit (GPU) and/or an image signal processor (ISP). The processor 210 may also include at least part of the components shown in FIG. 2, e.g., a cellular module 221. The processor 210 is capable of loading commands or data received from at least one of other components (e.g., a non-volatile memory) on a volatile memory, processing the loaded commands or data. The processor 210 is capable of storing various data in a non-volatile memory.

The communication module 220 may include the same or similar configurations as the communication interface 170 shown in FIG. 1. For example, the communication interface 170 is capable of including a cellular module 221, Wi-Fi module 223, BT module 225, GNSS module 227 (e.g., a GPS module, Glonass module, Beidou module or Galileo module), NFC module 228, and RF module 229.

The cellular module 221 is capable of providing a voice call, a video call, an SMS service, an Internet service, etc., through a communication network, for example. According to an embodiment, the cellular module 221 is capable of identifying and authenticating an electronic device 201 in a communication network by using a SIM 224 (e.g., a SIM card). According to an embodiment, the cellular module 221 is capable of performing at least part of the functions provided by the processor 210. According to an embodiment, the cellular module 221 is also capable of including a CP.

Each of the Wi-Fi module 223, the BT module 225, the GNSS module 227, and the NFC module 228 is capable of including a processor for processing data transmitted or received through the corresponding module. According to embodiments, at least part of the cellular module 221, Wi-Fi module 223, BT module 225, GNSS module 227, and NFC module 228 (e.g., two or more modules) may be included in one IC or one IC package.

The RF module 229 is capable of transmission/reception of communication signals, e.g., RF signals. The RF module 229 is capable of including a transceiver, a power amp module (PAM), a frequency filter, a low noise amplifier (LNA), an antenna, etc. According to another embodiment, at least one of the following modules: cellular module 221, Wi-Fi module 223, BT module 225, GNSS module 227, and NFC module 228 is capable of transmission/reception of RF signals through a separate RF module.

The SIM module 224 is capable of including a card including a SIM and/or an embedded SIM. The SIM module 224 is also capable of containing unique identification information, e.g., integrated circuit card identifier (ICCID), or subscriber information, e.g., international mobile subscriber identity (IMSI).

The memory 230 (e.g., memory 130 shown in FIG. 1) is capable of including an internal memory 232 or an external memory 234. The internal memory 232 is capable of including at least one of the following: a volatile memory, e.g., a dynamic RAM (DRAM), a static RAM (SRAM), a synchronous dynamic RAM (SDRAM), etc.; and a non-volatile memory, e.g., a one-time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash memory, an NOR flash memory, etc.), a hard drive, a solid state drive (SSD), etc.

The external memory 234 is also capable of including a flash drive, e.g., a compact flash (CF), a secure digital (SD), a micro SD (Micro-SD), a mini SD (Mini-SD), an extreme digital (xD), a multi-media card (MMC), a memory stick, etc. The external memory 234 is capable of being connected to the electronic device 201, functionally and/or physically, through various interfaces.

The sensor module 240 is capable of measuring/detecting a physical quantity or an operation state of the electronic device 201, and converting the measured or detected information into an electronic signal. The sensor module 240 is capable of including at least one of the following: a gesture sensor 240A, a gyro sensor 240B, an barometer sensor 240C, a magnetic sensor 240D, an acceleration sensor 240E, a grip sensor 240F, a proximity sensor 240G, a color sensor 240H (e.g., a red, green and blue (RGB) sensor), a biometric sensor 240I, a temperature/humidity sensor 240J, an illuminance sensor 240K, a ultraviolet (UV) sensor 240M, and infrared ray (IR) sensor 240N. Additionally or alternatively, the sensor module 240 is capable of further including an E-nose sensor, an electromyography (EMG) sensor, an electroencephalogram (EEG) sensor, an electrocardiogram (ECG) sensor, an IR sensor, an iris sensor and/or a fingerprint sensor. The sensor module 240 is capable of further including a control circuit for controlling one or more sensors included therein. In embodiments, the electronic device 201 is capable of including a processor, configured as part of the processor 210 or a separate component, for controlling the sensor module 240. In this case, while the processor 210 is operating in sleep mode, the processor is capable of controlling the sensor module 240.

The input device 250 is capable of including a touch panel 252, a (digital) pen sensor 254, a key 256, or an ultrasonic input device 258. The touch panel 252 may be implemented with at least one of the following: a capacitive touch system, a resistive touch system, an infrared touch system, and an ultrasonic touch system. The touch panel 252 may further include a control circuit. The touch panel 252 may also further include a tactile layer to provide a tactile response to the user.

The (digital) pen sensor 254 may be implemented with a part of the touch panel or with a separate recognition sheet. The key 256 may include a physical button, an optical key, or a keypad. The ultrasonic input device 258 is capable of detecting ultrasonic waves, created in an input tool, through a microphone 288, and identifying data corresponding to the detected ultrasonic waves.

The display 260 (e.g., the display 160 shown in FIG. 1) is capable of including a panel 262, a hologram unit 264, or a projector 266. The panel 262 may include the same or similar configurations as the display 160 shown in FIG. 1. The panel 262 may be implemented to be flexible, transparent, or wearable. The panel 262 may also be incorporated into one module together with the touch panel 252. The hologram unit 264 is capable of showing a stereoscopic image in the air by using light interference. The projector 266 is capable of displaying an image by projecting light onto a screen. The screen may be located inside or outside of the electronic device 201. According to an embodiment, the display 260 may further include a control circuit for controlling the panel 262, the hologram unit 264, or the projector 266.

The interface 270 is capable of including a HDMI 272, a USB 274, an optical interface 276, or a d-subminiature (D-sub) 278. The interface 270 may be included in the communication interface 170 shown in FIG. 1. Additionally or alternatively, the interface 270 is capable of including a mobile high-definition link (MHL) interface, a SD card/MMC card interface, or an infrared data association (IrDA) standard interface.

The audio module 280 is capable of providing bidirectional conversion between a sound and an electronic signal. At least part of the components in the audio module 280 may be included in the input/output interface 150 shown in FIG. 1. The audio module 280 is capable of processing sound information input or output through a speaker 282, a receiver 284, earphones 286, microphone 288, etc.

The camera module 291 refers to a device capable of taking both still and moving images. According to an embodiment, the camera module 291 is capable of including one or more image sensors (e.g., a front image sensor or a rear image sensor), a lens, an ISP, a flash (e.g., an LED or xenon lamp), etc.

The power management module 295 is capable of managing power of the electronic device 201. According to an embodiment, the power management module 295 is capable of including a power management integrated circuit (PMIC), a charger IC, or a battery or fuel gauge. The PMIC may employ wired charging and/or wireless charging methods. Examples of the wireless charging method are magnetic resonance charging, magnetic induction charging, and electromagnetic charging. To this end, the PIMC may further include an additional circuit for wireless charging, such as a coil loop, a resonance circuit, a rectifier, etc. The battery gauge is capable of measuring the residual capacity, charge in voltage, current, or temperature of the battery 296. The battery 296 takes the form of either a rechargeable battery or a solar battery.

The indicator 297 is capable of displaying a specific status of the electronic device 201 or a part thereof (e.g., the processor 210), e.g., a boot-up status, a message status, a charging status, etc. The motor 298 is capable of converting an electrical signal into mechanical vibrations, such as, a vibration effect, a haptic effect, etc. Although not shown, the electronic device 201 is capable of further including a processing unit (e.g., GPU) for supporting a mobile TV. The processing unit for supporting a mobile TV is capable of processing media data pursuant to standards, e.g., digital multimedia broadcasting (DMB), digital video broadcasting (DVB), or mediaFlo™, etc.

Figure 3:
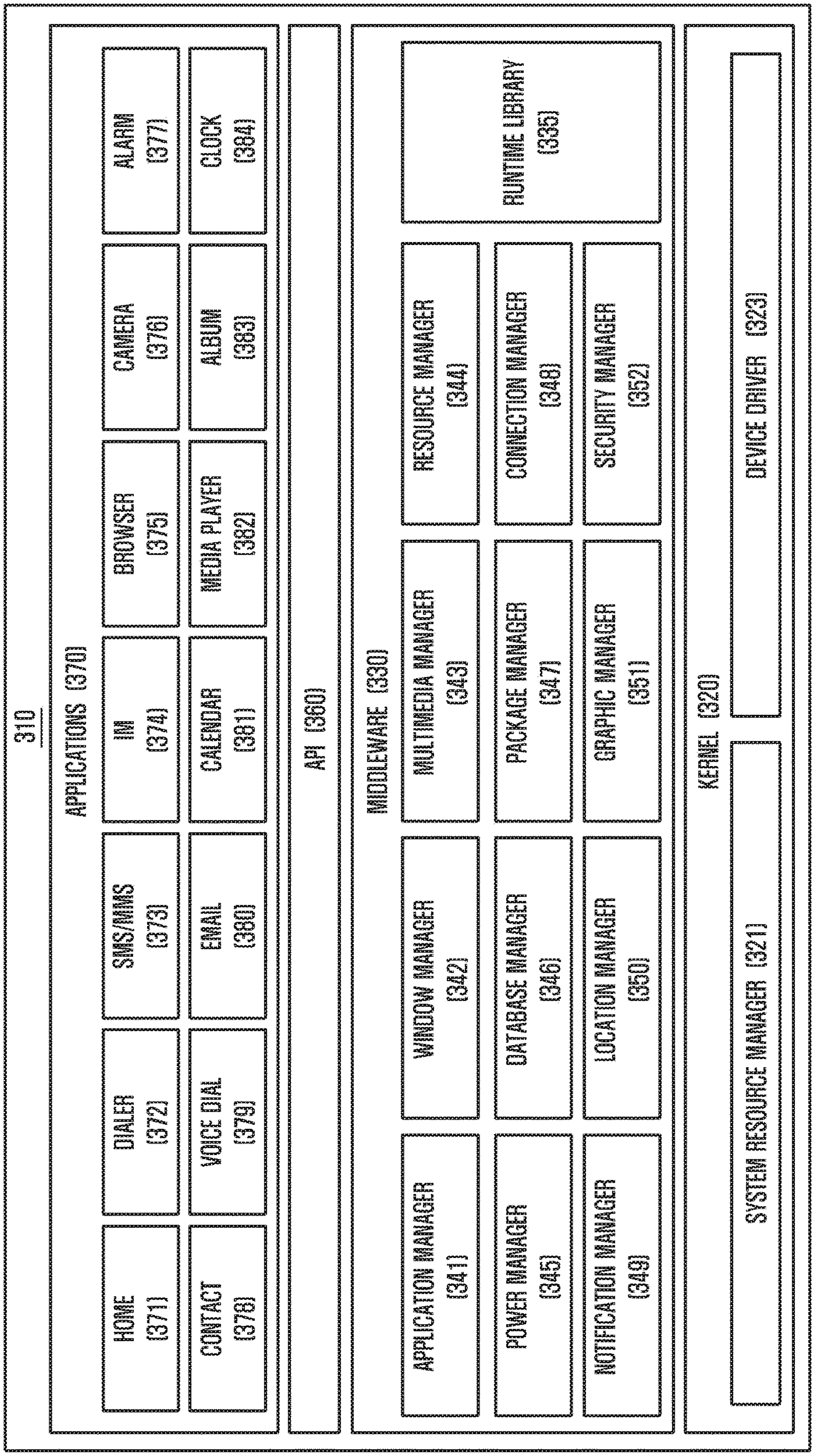
FIG. 3 is a block diagram illustrating the configuration of a program module according to an embodiment of the present disclosure.

FIG. 3 is a block diagram of a programming module according to various embodiments.

Referring to FIG. 3, the program module 310 (e.g., program module 140 shown in FIG. 1) is capable of including an OS for controlling resources related to the electronic device (e.g., electronic device 101) and/or various applications (e.g., application programs 147 shown in FIG. 1) running on the OS. The OS may be Android, iOS, Windows, Symbian, Tizen, Bada, etc.

The program module 310 is capable of including a kernel 320, middleware 330, API 360 and/or applications 370. At least part of the program module 310 may be preloaded on the electronic device or downloaded from a server (e.g., an electronic device 102 or 104, server 106, etc.).

The kernel 320 (for example, kernel 141) may include a system resource manager 321 and/or a device driver 323. The system resource manager 321 may include, for example, a process manager, a memory manager, and a file system manager. The system resource manager 321 may perform a system resource control, allocation, and recall. The device driver 323 may include, for example, a display driver, a camera driver, a BT driver, a shared memory driver, a USB driver, a keypad driver, a Wi-Fi driver, and an audio driver. Further, according to an embodiment, the device driver 323 may include an inter-process communication (IPC) driver.

The middleware 330 may provide a function required in common by the applications 370. Further, the middleware 330 may provide a function through the API 360 to allow the applications 370 to efficiently use limited system resources within the electronic device. According to an embodiment, the middleware 330 (for example, the middleware 143) may include at least one of a runtime library 335, an application manager 341, a window manager 342, a multimedia manager 343, a resource manager 344, a power manager 345, a database (DB) manager 346, a package manager 347, a connection manager 348, a notification manager 349, a location manager 350, a graphic manager 351, and a security manager 352.

The runtime library 335 may include, for example, a library module used by a complier to add a new function through a programming language while the applications 370 are executed. According to an embodiment, the runtime library 335 executes input and output, management of a memory, a function associated with an arithmetic function and the like.

The application manager 341 may manage, for example, a life cycle of at least one of the applications 370. The window manager 342 may manage GUI resources used on the screen. The multimedia manager 343 may detect a format required for reproducing various media files and perform an encoding or a decoding of a media file by using a codec suitable for the corresponding format. The resource manager 344 manages resources such as a source code, a memory, or a storage space of at least one of the applications 370.

The power manager 345 may manage, for example, battery capacity, temperature, or power, and may determine or provide power information that is necessary for the operation of an electronic device using the corresponding information.

The power manager 345 may operate together with a basic input/output system (BIOS) to manage a battery or power and provides power information required for the operation. The DB manager 346 may manage generation, search, and change of a DB to be used by at least one of the applications 370. The package manager 347 may manage an installation or an update of an application distributed in a form of a package file.

The connection manager 348 may manage, for example, a wireless connection such as Wi-Fi or BT. The notification manager 349 may display or notify a user of an event such as an arrival message, an appointment, a proximity alarm or the like, in a manner that does not disturb the user. The location manager 350 may manage location information of the electronic device. The graphic manager 351 may manage a graphic effect provided to the user or a user interface related to the graphic effect. The security manager 352 provides a general security function required for a system security or a user authentication. According to an embodiment, when the electronic device (for example, the electronic device 101) has a call function, the middleware 330 may further include a telephony manager for managing a voice of the electronic device or a video call function.

The middleware 330 is capable of including modules configuring various combinations of functions of the above described components. The middleware 330 is capable of providing modules specialized according to types of operation systems to provide distinct functions. The middleware 330 may be adaptively configured in such a way as to remove part of the existing components or to include new components.

The API 360 (for example, API 145) may be a set of API programming functions, and may be provided with a different configuration according to an operating system. For example, in Android or iOS, a single API set may be provided for each platform. In Tizen, two or more API sets may be provided.

The applications 370 (e.g., application programs 147) may include one or more applications for performing various functions, e.g., home 371, dialer 372, SMS/MMS 373, instant message (IM) 374, browser 375, camera 376, alarm 377, contact 378, voice dial 379, email 380, calendar 381, media player 382, album 383, clock 384, health care (e.g., an application for measuring amount of exercise, blood sugar level, etc.), and environment information (e.g., an application for providing atmospheric pressure, humidity, temperature, etc.).

According to an embodiment, the applications 370 are capable of including an application for supporting information exchange between an electronic device (e.g., electronic device 101) and an external device (e.g., electronic devices 102 and 104), which is hereafter called 'information exchange application'). The information exchange application is capable of including a notification relay application for relaying specific information to external devices or a device management application for managing external devices.

For example, the notification relay application is capable of including a function for relaying notification information, created in other applications of the electronic device (e.g., SMS/MMS application, email application, health care application, environment information application, etc.) to external devices (e.g., electronic devices 102 and 104). In addition, the notification relay application is capable of receiving notification information from external devices to provide the received information to the user.

The device management application is capable of managing (e.g., installing, removing or updating) at least one function of an external device (e.g., electronic devices 102 and 104) communicating with the electronic device. Examples of the function are a function of turning-on/off the external device or part of the external device, a function of controlling the brightness (or resolution) of the display, applications running on the external device, services provided by the external device, etc. Examples of the services are a call service, messaging service, etc.

According to an embodiment, the applications 370 are capable of including an application (e.g., a health care application of a mobile medical device, etc.) specified attributes of an external device (e.g., electronic devices 102 and 104). According to an embodiment, the applications 370 are capable of including applications received from an external device (e.g., a server 106, electronic devices 102 and 104). According to an embodiment, the applications 370 are capable of including a preloaded application or third party applications that can be downloaded from a server. It should be understood that the components of the program module 310 may be called different names according to types of operating systems.

According to various embodiments, at least part of the program module 310 can be implemented with software, firmware, hardware, or any combination of two or more of them. At least part of the program module 310 can be implemented (e.g., executed) by a processor (e.g., processor 210). At least part of the programming module 310 may include modules, programs, routines, sets of instructions or processes, etc., in order to perform one or more functions.

The term "module" used in this disclosure may refer to a certain unit that includes one of hardware, software and firmware or any combination thereof. The module may be interchangeably used with unit, logic, logical block, component, or circuit, for example. The module may be the minimum unit, or part thereof, which performs one or more particular functions. The module may be formed mechanically or electronically. For example, the module disclosed herein may include at least one of application-specific integrated circuit (ASIC) chip, field-programmable gate arrays (FPGAs), and programmable-logic device, which have been known or are to be developed.

Figure 4:
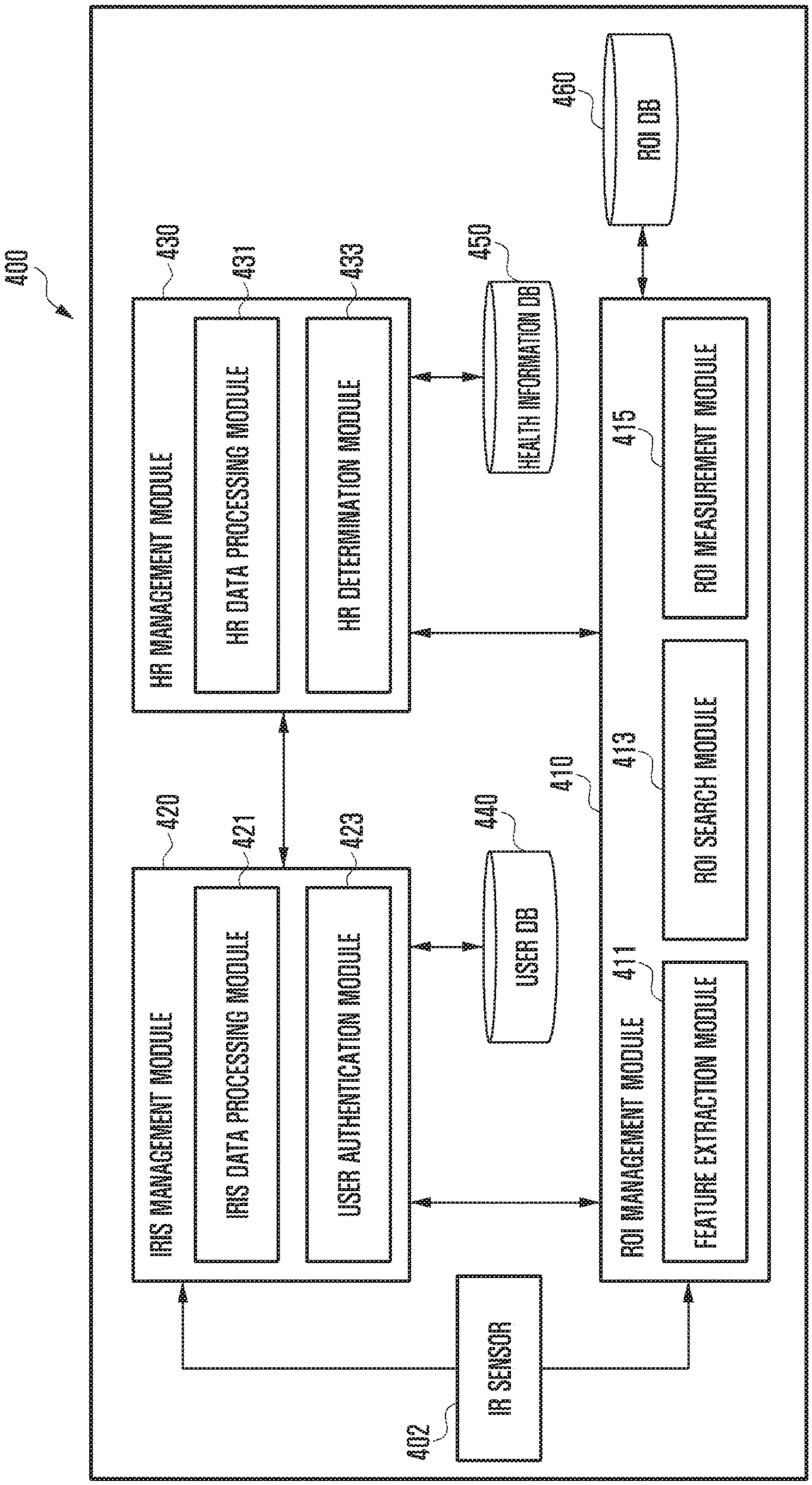
FIG. 4 is a diagram illustrating the configuration of an electronic device that manages HR information and iris information that are acquired using an IR sensor according to an embodiment of the present disclosure.

FIG. 4 is a diagram illustrating the configuration of an electronic device that manages HR information and iris information that are acquired using an IR sensor according to an embodiment of the present disclosure.

Referring to FIG. 4, a processor (e.g., processor 210 of FIG. 2) of an electronic device 400 (e.g., electronic device 201 of FIG. 2) may include a region of interest (ROI) management module 410, an iris management module 420, and a heart rate (HR) management module 430, and may control the ROI management module 410, the iris management module 420, and the HR management module 430.

According to various embodiments, the electronic device 400 may acquire raw data using an infrared rays (IR) sensor 402 (IR sensor 240N of FIG. 2, hereinafter referred to as an "IR sensor"). Here, the IR sensor 402 may be a sensor that is built in the electronic device as one constituent element (sensor) that includes a light emitting unit and a light receiving unit. According to various embodiments, the IR sensor 402 may be a sensor that is built in a camera (camera module 291 of FIG. 2) that is provided in the electronic device 400. In various embodiments of the present disclosure, several sensors or modules may be associated with each other to operate as one sensor. According to various embodiments, the IR sensor 402 may be composed of a light emitting unit to operate as the light emitting unit, or may be associated with a light receiving unit of the camera to operate as one IR sensor. As described above, the IR sensor 402 according to various embodiments of the present disclosure may be configured in diverse manners.

According to various embodiments, the quantity of light of the IR sensor 402 may be adjusted in accordance with the use purpose of the IR sensor 402 or the distance between a user and the IR sensor 402. The quantity of light of the IR sensor 402 may be optimized based on the use purpose of the IR sensor 402 or the distance between the user and the IR sensor 402. According to various embodiments, the IR sensor 402 may operate using a predetermined optimum quantity of light to correspond to the use purpose of the IR sensor or the distance between the user and the IR sensor 402.

According to various embodiments, in the case of performing iris authentication and HR measurement using an IR sensor having the maximum current value of 1.5 A, there may be experimental results as disclosed in the following Table 1.

TABLE 1

| Purpose | Current | Intensity of radiation | Temperature | Distance |
|---|---|---|---|---|
| Authentication of iris | About 950 mA | About 1662.5 mW/sr | 25° C. | About 10~30 cm |
| Measurement of a HR | About 200 mA~600 mA | About 350 mW/sr~1050 mW/sr | 25° C. | About 10~30 cm |
| Eye tracker (gazing) | About 200 mA~ | About 350 mW/sr | 25° C. | About 10 cm~ |

Referring to the above-described Table, the IR sensor 402 according to various embodiments may authenticate an iris, measure a HR, or perform eye tracking (gazing). According to various embodiments, if the IR sensor 402 operates as an eye tracker, it may grasp the location of the pupil of the eye, and may track what the pupil is seeing, and whether the eye is opened or closed. According to various embodiments, an optimum current value and the quantity of light of the IR sensor 402 may be determined in accordance with the use purpose of the IR sensor or the distance between the IR sensor and a measurement target for which the IR sensor is to be used.

According to various embodiments, in the case of authenticating an iris through an IR sensor 402 at a point that is apart for about 10 to 30 cm from the iris, the IR sensor 402 may require current of about 950 mA. According to various embodiments, the electronic device 400 may determine the optimum distance for authenticating the iris, and may determine the current in consideration of the quantity of light that can secure accuracy of the iris authentication and safety of the eye (iris). The optimum current value for authenticating the iris in a distance of about 10 to 30 cm may be 950 mA. In other words, in the case where the IR sensor 402 operates with the current of 950 MA, the accuracy of the iris authentication that corresponds to the iris which is located in a distance that is apart for about 10 to 30 cm from the iris becomes maximized, and the IR sensor operates based on the quantity of light that can safely protect the eye (iris). On the other hand, if the IR sensor 402 operates with current that is higher than 950 mA to authenticate the iris in the distance of about 10 to 30 cm, the quantity of light of the IR sensor becomes saturated. Accordingly, the measurement value for the iris authentication may not be accurate, and it may be difficult to safely protect the eye (iris). Further, if the IR sensor 402 operates with current that is lower than 950 mA, the accuracy of the iris authentication may be degraded, and thus it may be difficult to use the IR sensor as an iris authentication means.

According to various embodiments, in the case of measuring a HR through the IR sensor 402 at a point that is apart for about 10 to 30 cm from a HR measurement point, the IR sensor 402 may require current of about 200 to 600 mA. According to various embodiments, the electronic device 400 may measure the HR in a distance that is apart for about 10 to 30 cm, and it may determine the optimum current value based on the distance apart. According to various embodiments, if the IR sensor for measuring the HR operates with the current of about 600 mA, the accuracy of the HR measurement that corresponds to a HR measurement point that is apart for about 30 cm from the electronic device 400 may be maximized.

According to various embodiments, if the IR sensor 402 is used for the purpose of an eye tracker at a point that is apart for about 10 cm from the eye of a user, the electronic device 400 may drive the IR sensor 402 with the current that is equal to or higher than about 200 mA in order to track the movement of the pupil of the user. According to various embodiments, as the electronic device 400 operates the IR sensor with the current that is equal to or higher than about 200 mA at the point that is apart for about 10 cm or more, the accuracy of tracking of the movement of the pupil of the user may be maximized.

According to various embodiments, there may be various methods for measuring a distance between the IR sensor 402 and the measurement target (e.g., iris or HR measurement point). According to various embodiments, the electronic device 400 may detect a user's face using an image sensor, and may determine an average value of pixels that correspond to the face. The electronic device 400 may determine the distance from the user based on the determined average value, and may control the current value and the quantity of light of the IR sensor corresponding to the distance. According to various embodiments, the electronic device 400 may protect the user's eye through adjustment of the quantity of light of the IR sensor based on the use purpose and the distance from the measurement target.

According to various embodiments, the electronic device 400 may preset the optimum current value and quantity of light that correspond to the use purpose and the distance from the measurement target, and may store the preset optimum current value and quantity of light in a memory.

According to various embodiments, the processor (e.g., processor 210 of FIG. 2) of the electronic device 400 may photograph any one object using the IR sensor 402, and may acquire raw data from the photographed object. The processor 210 of the electronic device 400 may extract features of the object based on the acquired raw data, and may search for a ROI based on the extracted features. Here, the features of the object may be constituent elements that constitute the object. According to various embodiments, if the object is a user's face, the features of the object may include eyes, a nose, a mouth, and a forehead that constitute the face. The electronic device 400 may acquire HR information and iris information of the object based on the searched ROI. The electronic device 400 may perform a specific function utilizing the acquired HR information and iris information.

According to various embodiments, the electronic device 400 may receive data of the object (e.g., user) using the IR sensor 402. In order to measure the HR of the user, the electronic device 400 may transmit the data that is received through the IR sensor 402 to the ROI management module 410. Further, in order to authenticate the user, the electronic device 400 may transmit the data that is received through the IR sensor 402 to the iris management module 420.

According to various embodiments, the electronic device 400 may include the ROI management module 410, and the ROI management module 410 may include a feature extraction module 411, an ROI search module 413, and an ROI measurement module 415.

According to various embodiments, the feature extraction module 411 may extract the features of the object based on the raw data that is acquired through the IR sensor 402. According to various embodiments, if the object is the user's face, the raw data may include data for recognizing the user's face. The raw data may include data for discriminating a face direction and a face location. The raw data may include data for determining the face shape and data for determining locations of eyes, a nose, a mouth, and a forehead in a face. That is, the feature extraction module 411 may determine the locations of the eyes, the nose, the mouth, and the forehead of the object based on the raw data of the object. In the above description, the object is exemplified as the user's face, but is not limited thereto. The object may include all body regions from which the HR can be measured using the IR sensor.

According to various embodiments, the ROI search module 413 may search for the ROI based on the locations of the eyes, nose, mouth, and forehead that are determined through the feature extraction module 411. Here, the ROI may include a specific area for measuring the HR of the object. Various embodiments of the present disclosure may sense image changes at specific locations (e.g., forehead, head temples, bags under eyes, and bag under a nose) based on the user's face, and may measure the HR of the user based on the image changes. Further, various embodiments of the present disclosure may sense image changes at specific locations (e.g., ear root, ear lobe, head temple, and bag under an eye) based on the side face of the user, and may measure the HR of the user based on the image changes. The ROI may be determined based on the locations of the eye, the nose, and the mouth that are determined through the feature extraction module 411, or may be determined as a predetermined ROI corresponding to the user. The ROI search module 413 may search for at least one ROI for measuring the HR of the object. The ROI search module 413 may perform the above-described operation in real time.

According to various embodiments, the ROI measurement module 415 may measure data of at least one ROI that is searched for through the ROI search module 413, or may measure data of at least one ROI that is pre-stored. According to various embodiments, the electronic device 400 may photograph or take an image of the ROI that is determined through the ROI search module 413. Here, the ROI measurement module 415 may measure at least one piece of ROI data, and may perform HR conversion simultaneously with the measurement of the ROI data. Further, the ROI measurement module 415 may perform filtering of data having a severe noise among the at least one piece of ROI data. The ROI measurement module 415 may calculate an average value or may select data for deriving the optimum value based on the at least one piece of ROI data.

According to various embodiments, if the ROI data (data for measuring the HR) gets out of a specific threshold value region or if it is difficult to measure the ROI data due to a lot of noise, the ROI measurement module 415 may request the ROI search module 413 to re-search for the ROI.

According to various embodiments, the ROI measurement module 415 may primarily filter or process the ROI data, and may transfer the corresponding information to the HR management module 430.

According to various embodiments, the ROI management module 410 may sense image changes in the searched ROI (e.g., forehead, head temples, and bags under eyes of the object), and may acquire HR data for measuring the HR of the object based on the sensed image changes. The ROI measurement module 415 may primarily filter or process the acquired HR data, and may transmit the processed data to the HR management module 430. Further, the ROI management module 410 may acquire the iris data of the object based on the eye location of the object that is determined through the feature extraction module 411. Further, the ROI measurement module 415 may transmit the acquired iris data to the iris management module 420.

According to various embodiments, the ROI management module 410 may manage ROI DB 460. According to various embodiments, the ROI management module 410 may store information that corresponds to the locations of the eyes, nose, mouth, and forehead of the object in the ROI DB 460. According to various embodiments, if a specific user (e.g., first user) is authenticated through a user authentication process, the ROI management module 410 may store ROI information that corresponds to the authenticated first user in the ROI DB 460. If the first user is authenticated thereafter, the ROI management module 410 may load the ROI information that is stored in the ROI DB 460 to correspond to the first user without an ROI searching process, and may acquire the HR data of the first user based on the loaded ROI information.

According to various embodiments, the electronic device 400 may include the iris management module 420, and the iris management module 420 may include an iris data processing module 421 and a user authentication module 423. The iris management module 420 may receive determined data (e.g., iris recognition data) using the IR sensor 402. Further, the iris management module 420 may receive iris data from the ROI management module 410. According to various embodiments, if iris-related data that is enough to perform user authentication can be acquired, the iris management module 420 may receive the iris data through the ROI management module 410. Further, the iris management module 420 may manage a user DB 440.

According to various embodiments, the iris data processing module 421 of the iris management module 420 may process the iris data that is received from the ROI management module 410. The iris management module 420 may authenticate a user based on the processed iris data, or may update iris information that is stored in the user DB 440 based on the iris data. According to various embodiments, the iris management module 420 may store information that corresponds to the user in the user DB 440.

According to various embodiments, if the iris data is received from the ROI management module 410, the user authentication module 423 of the iris management module 420 may perform the user authentication through comparison of the received iris data with the iris data that is stored in the user DB 440. Further, if an additional authentication is necessary, the iris management module 420 may request information related to a HR of the object from the HR management module 430. Further, the iris management module 420 may update the user DB 440 based on information that is used to authenticate a specific user.

According to various embodiments, the electronic device 400 may include the HR management module 430, and the HR management module 430 may include a HR data processing module 431 and a HR determination module 433. The HR management module 430 may receive HR data from the ROI management module 410. Further, the HR management module 430 may manage a health information DB.

According to various embodiments, the HR data processing module 431 of the HR management module 430 may process ROI data that is received from the ROI management module 410. According to various embodiments, the ROI measurement module 415 of the ROI management module 410 may primarily filter or process the ROI data. Further, the ROI management module 410 may transfer the primarily processed ROI data to the HR management module 430. The HR data processing module 431 of the HR management module 430 may convert (secondarily process) the primarily processed ROI data into HR data. According to various embodiments, the HR data processing module 431 may receive only data that is measured from the bags under the eyes of the object (user), and may convert the received data into the HR data. Further, the HR data processing module 431 may receive plural pieces of data that are measured from the bags under the eyes and the head temples, calculate an average value of the plural pieces of data, and then convert the average value into one piece of HR data. That is, the HR data processing module 431 may calculate the average value based on data values that are extracted from N or more ROI regions, and may convert the average value into one piece of HR data. Further, the HR data processing module 431 may provide one piece of HR data based on the optimum ROI (e.g., ROI in which no noise occurs) through a noise filtering process.

According to various embodiments, the HR determination module 433 may determine an expected HR of the object based on the converted HR data. According to various embodiments, the ROI management module 410 may acquire plural pieces of HR data based on the plural ROI regions, and may transmit the acquired pieces of HR data to the HR management module 430. The HR management module 430 may calculate an average value of the HR data based on the acquired pieces of HR data. The HR management module 430 may determine the expected HR of the object based on the average value of the HR data.

According to various embodiments, the HR management module 430 may compare the determined expected HR with the HR information that is stored in the health information DB 450, and may provide information on the result of the comparison to the user. According to various embodiments, if the determined expected HR is higher than the HR in a normal state, the HR management module 430 may provide information on the HR through a user interface (e.g., color change of the user interface and display of a guide message for performing a specific operation). Further, the HR management module 430 may update the HR information that is stored in the health information DB 450 based on the determined expected HR.

According to various embodiments of the present disclosure, an electronic device may include an IR sensor, a memory, and a processor electrically connected to the IR sensor and the memory, wherein the memory stores instructions which, when executed, cause the processor to receive an image using the IR sensor, to determine at least one ROI for measuring a HR in the received image, and to determine the HR based on the at least one determined ROI.

According to various embodiments, the electronic device may detect an object from the received image, extract features of the detected object, and determine the at least one ROI based on the extracted features of the object.

According to various embodiments, the electronic device may extract locations of eyes, a nose, a mouth, and a forehead of a user as the features if a user's face is included in the received image.

According to various embodiments, the electronic device may receive a request for user authentication, recognize an iris of a user using the IR sensor, determine whether measurement of the HR is possible in the ROI, and complete the user authentication if the HR is measured.

According to various embodiments, the electronic device may determine the HR of the user based on the determined ROI if the ROI is determined to correspond to the authenticated user.

According to various embodiments, the electronic device may store the at least one determined ROI in the memory to correspond to the authenticated user if the ROI is not determined to correspond to the authenticated user.

According to various embodiments, the electronic device may measure a noise that occurs in the at least one ROI, and may exclude the ROI from a candidate group of ROI in which measurement of the HR is possible if the measured noise exceeds a predetermined threshold value.

According to various embodiments, the electronic device may determine the HR based on the candidate group of ROI in which the measurement of the HR is possible.

According to various embodiments, the electronic device may receive data for measuring the HR from the at least one determined ROI, convert the received data into HR data, and determine the converted HR data as the HR.

According to various embodiments, the electronic device may receive data that corresponds to an image change in the at least one determined ROI, and may convert the received data into the HR to determine the HR.

According to various embodiments, the electronic device may control the quantity of light of the IR sensor based on a use purpose of the IR sensor and a distance between an object and the IR sensor.

According to various embodiments, the IR sensor may be composed of any one of a sensor that includes both a light emitting unit and a light receiving unit, a sensor built in a camera, and a sensor in which a sensor that is a light emitting unit and a camera that is a light receiving unit are associated with each other.

Figure 5:
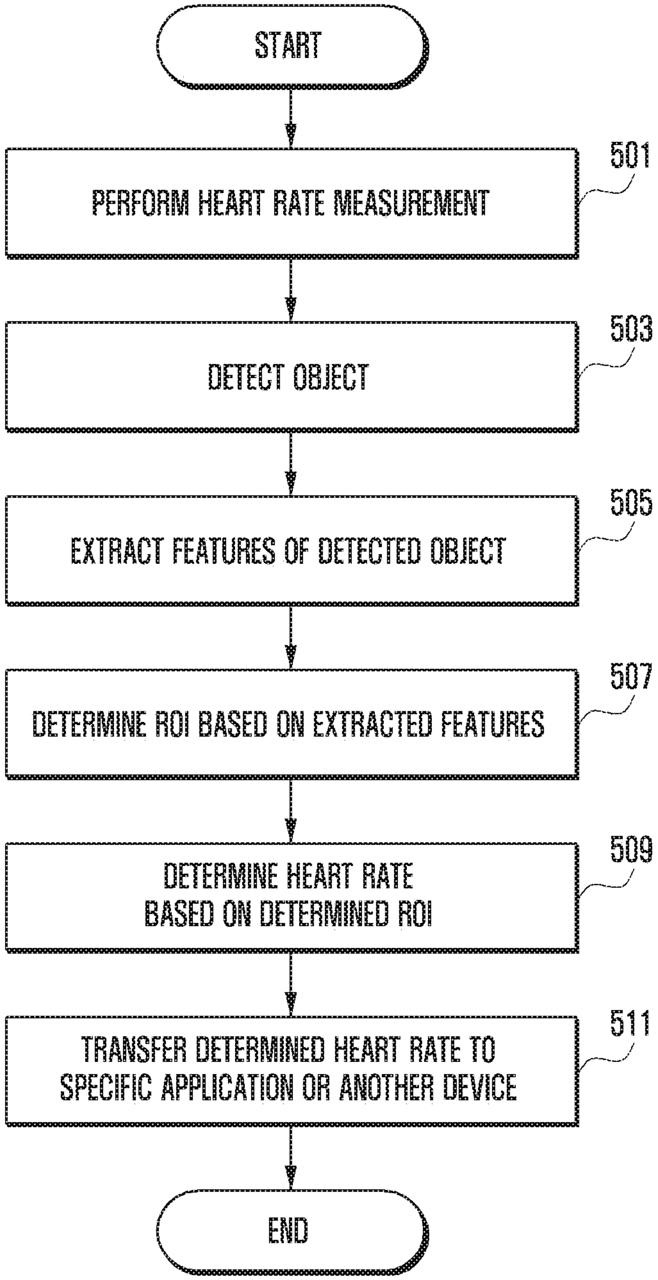
FIG. 5 is a flowchart illustrating a method for measuring a HR using an IR sensor according to an embodiment of the present disclosure.

FIG. 5 is a flowchart illustrating a method for measuring a HR using an IR sensor according to an embodiment of the present disclosure.

Referring to FIG. 5, at operation 501, an electronic device (electronic device 400 of FIG. 4) may perform HR measurement. According to various embodiments, the electronic device 400 may perform the HR measurement corresponding to an execution of an application program. Further, if a HR measurement command is received from a user, the electronic device 400 may perform the HR measurement. Whether to perform the HR measurement may be determined by a user setup.

At operation 503, the electronic device 400 may detect an object (e.g., user). According to various embodiments, the electronic device 400 may detect the object using an IR sensor (e.g., IR sensor 402 of FIG. 4) or a camera. At operation 505, the electronic device 400 may extract features of the detected object. According to various embodiments, if the object corresponds to a user's face, the electronic device 400 may sense a region in which eyes, a nose, and a mouth are located based on the determined face shape of the user, and may accurately extract the locations of the eyes, nose, and mouth of the user based on the sensed region.

At operation 507, the electronic device 400 may determine a ROI based on the extracted features. Here, the ROI may include a forehead, head temples, and bags under eyes of the user. The ROI may be at least one face feature region (area) (e.g., forehead, head temples, and bags under eyes) in which the user's HR data can be acquired using the IR sensor. According to various embodiments, the electronic device 400 may sense an image change in the ROI using the IR sensor, and may acquire the HR data based on the sensed image change. That is, the ROI may be a specific area in which the HR can be measured or the image change occurs. The ROI is not limited to the regions as described above. The electronic device 400 may determine the ROI based on the locations (features) of the eyes, the nose, the mouth, and the forehead.

At operation 509, the electronic device 400 may determine the HR based on the determined ROI. According to various embodiments, the electronic device 400 may sense the image change in the searched ROI, and may acquire the HR data based on the sensed image change. If a plurality of ROI regions are searched for, the electronic device 400 may acquire plural pieces of HR data, and may calculate an average value of the plural pieces of HR data being acquired to determine the HR of the user.

At operation 511, the electronic device 400 may transfer information on the determined HR to a specific application or another device (e.g., user's wearable device or another electronic device). According to various embodiments, the electronic device 400 may transmit the information on the determined HR to a health-related application in a predetermined period. Further, the electronic device 400 may transmit the information on the determined HR to the user's wearable device. The electronic device 400 may perform mapping of the determined HR on specific content, or may store the determined HR as metadata.

According to various embodiments, a specific application may provide the information on the HR to the user based on the information on the HR of the user. According to various embodiments, if the determined HR is higher than a normal HR (e.g., predetermined threshold value), the electronic device 400 may change the color of a user interface. The electronic device 400 may provide the information on the HR to the user through changing the color of the user interface to green. Further, the electronic device 400 may display a guide message (e.g., "Please take a break for a short time") through the user interface. The electronic device 400 may determine whether the user feels stressed based on the HR of the user, and may provide a health service in accordance with the result of the determination. Further, the electronic device 400 may continuously record the measured HR of the user, and may provide a service for analogizing the stress level and the vascular age of the user.

According to various embodiments, if the specific application is a gallery-related application, the electronic device 400 may include the HR information in an image that is stored in a gallery. Further, the electronic device 400 may list up and display the image based on the HR information. Further, if the HR that exceeds the predetermined threshold value is measured while the user is viewing a video image, the electronic device 400 may clip the video image at the corresponding time and may display the video image as thumbnail.

According to various embodiments, if iris authentication and HR measurement are simultaneously performed, the electronic device 400 may check liveness for the object (user) based on the measured HR, and may display through the interface the result of the checking (e.g., notification (message) information such as "Authentication completed" or "HR information has not been measured. Please perform re-authentication").

According to various embodiments, in the case of measuring a HR through a HMD device, it is not necessary for the HMD device that is provided with an IR sensor to come in contact with the skin of the user, and the HMD device may search for a ROI using the IR sensor and may sense an image change in the ROI. According to various embodiments, the HMD device that is provided with the IR sensor may detect bio information (e.g., iris information) of the user. According to various embodiments, the HMD device may sense the iris information of the user using the IR sensor, and may utilize the iris information of the user as data for authenticating the user.

According to various embodiments, in the case of measuring the HR through the HMD device, the HMD device may provide specific information to the user in accordance with a change of the HR. According to various embodiments, if the HR is increased in a state where the user wears the HMD device, the HMD device may provide the user with a notification message for inviting the user to get a rest. The HMD device may provide a service for change into peaceful music and background so that the HR of the user becomes calm.

Figure 6:
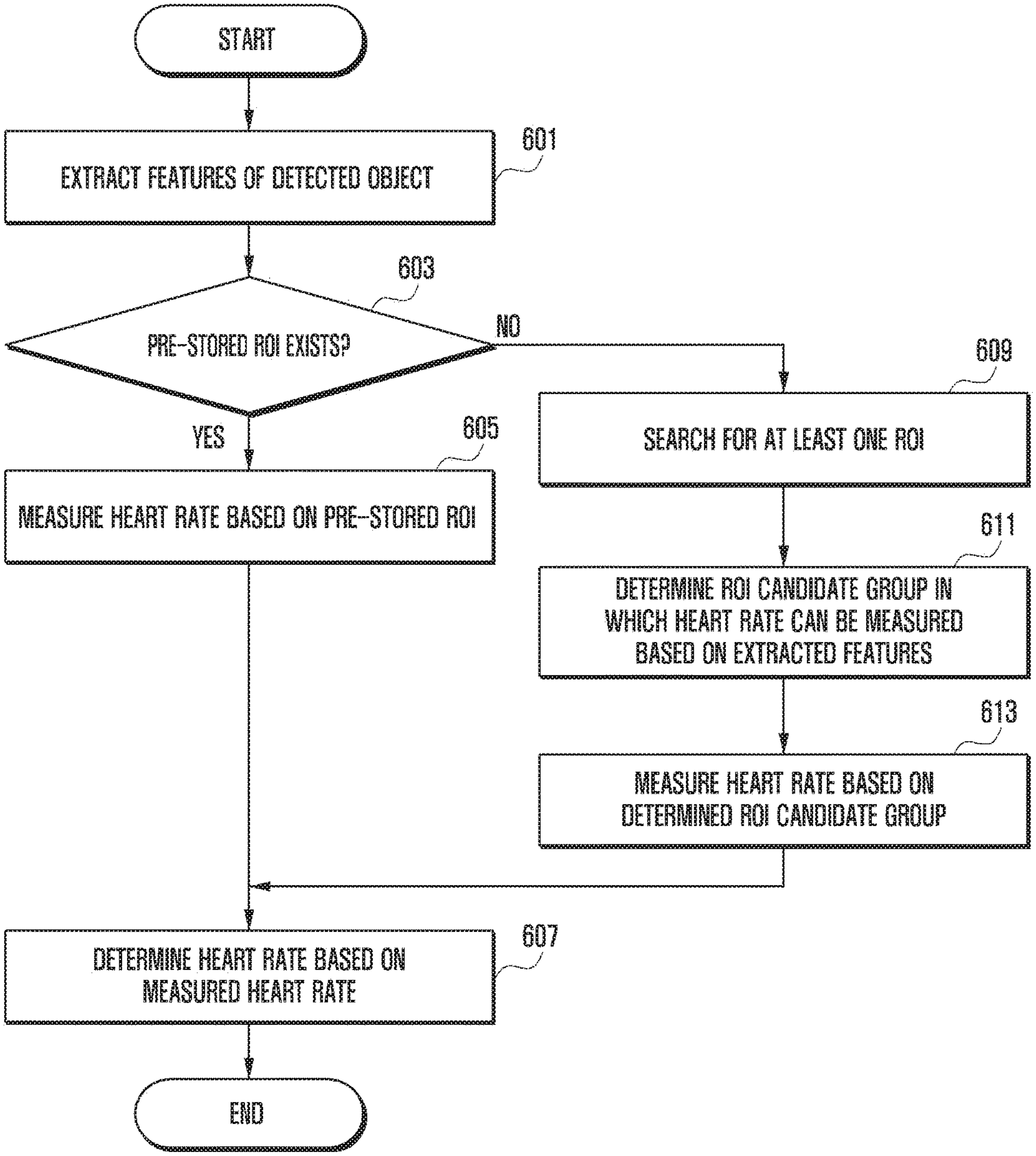
FIG. 6 is a flowchart illustrating a method for measuring a HR using an IR sensor, in which if there is a pre-stored ROI, the HR is measured based on the pre-stored ROI, whereas if there is not a pre-stored ROI, the HR is measured through searching for a ROI, according to an embodiment of the present disclosure.

FIG. 6 is a flowchart illustrating a method for measuring a HR using an IR sensor, in which if there is a pre-stored ROI, the HR is measured based on the pre-stored ROI, whereas if there is not a pre-stored ROI, the HR is measured through searching for a ROI, according to an embodiment of the present disclosure.

FIG. 6 is a flowchart illustrating subdivided operations explaining in more detail the operations 505 to 509 of FIG. 5. Referring to FIG. 6, at operation 601, a processor (processor 210 of FIG. 4) of an electronic device may extract features of a detected object. Operation 601 is equal to the operation 505 of FIG. 5. At operation 603, the processor 210 may determine whether there is a ROI that is pre-stored in the memory.

If the pre-stored ROI exists at operation 603, the processor 210, at operation 605, may measure a HR based on the pre-stored ROI. The processor 210 may select at least one pre-stored ROI, and may analyze an image that corresponds to the selected ROI. The processor 210 may determine the at least one ROI region in which the image is to be converted into the HR through the image analysis, and may measure the HR based on the determined ROI. At operation 607, the processor 210 may determine the HR based on the measured HR. If plural HRs are measured, the processor 210 may calculate an average value of the measured HRs, and may determine the average value as the HR.

If the pre-stored ROI does not exist at operation 603, the processor 210, at operation 609, may search for at least one ROI. According to various embodiments, if the object corresponds to a user's face, the processor 210 may search for the at least one ROI based on features of the user's face (e.g., features that correspond to locations of eyes, a nose, a mouth, and a forehead of the user). The processor 210 may search for a partial area of a forehead, head temples, and bags under eyes as the ROI regions in order to measure the HR based on the locations of the eyes, nose, mouth, and forehead of the user.

According to various embodiments, the processor 210 may measure a noise value that occurs in the searched ROI. According to various embodiments, the processor 210 may measure the noise value in a first ROI among the searched ROI regions. If the measured noise value exceeds a predetermined threshold value, the processor 210 may exclude the first ROI from a candidate group of ROI regions.

At operation 611, the processor 210 may determine a candidate group of ROI regions in which the HR can be measured based on the extracted features. The candidate group of ROI regions may include the ROI in which less noise occurs.

At operation 613, the processor 210 may measure the HR based on the determined candidate group of ROI regions. Further, at operation 607, the processor 210 may determine the HR based on the measured HR.

According to various embodiments, if user authentication has been performed, the electronic device may store the ROI in which the HR can be measured to correspond to the authenticated user in an ROI DB (ROI DB 460 of FIG. 4). Thereafter, if the HR measurement is performed in a state where the user authentication has been performed, the processor 210 may omit a process of searching for the ROI. The processor 210 may determine the ROI that is stored in the ROI DB 460 to correspond to the authenticated user, and may measure the HR of the user based on the determined ROI.

Figure 7:
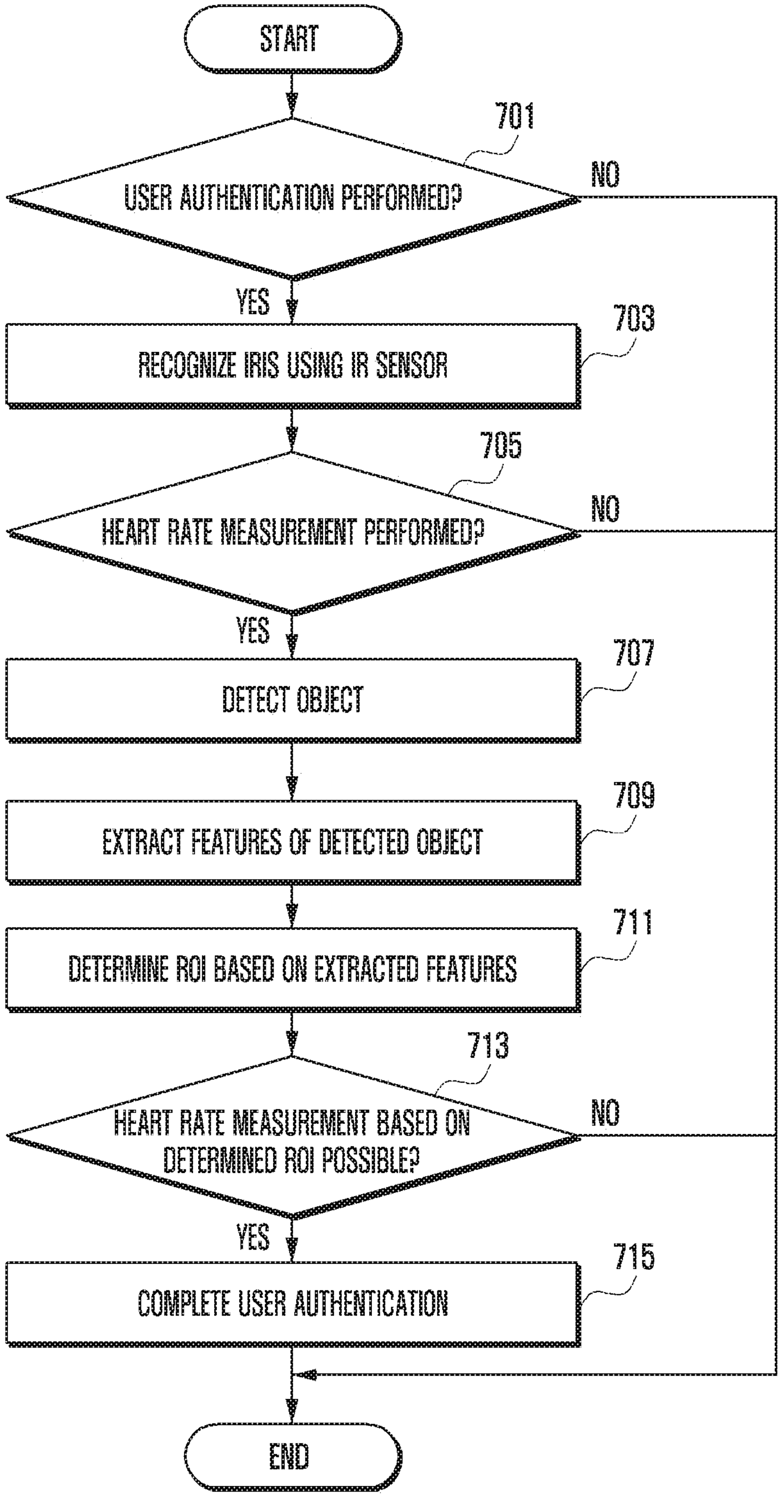
FIG. 7 is a flowchart illustrating a method for authenticating a user using an IR sensor according to an embodiment of the present disclosure.

FIG. 7 is a flowchart illustrating a method for authenticating a user using an IR sensor according to an embodiment of the present disclosure.

Referring to FIG. 7, at operation 701, a processor (processor 210 of FIG. 4) of an electronic device may determine whether user authentication has been performed. If the user authentication has been performed, at operation 703, the processor 210 may recognize an iris of a user using an IR sensor. Various embodiments of the present disclosure may perform HR measurement while recognizing the iris for the user authentication. Various embodiments of the present disclosure may perform iris authentication, and may complete the user authentication if the HR measurement is possible. Since various embodiments of the present disclosure determine whether to perform the HR measurement together with the iris authentication, the performance of the user authentication can be more strengthened. Various embodiments of the present disclosure can prevent the user authentication from being performed only with an iris image of a specific user that may be copied.

At operation 705, the processor 210 may determine whether to perform the HR measurement. In the case of performing the HR measurement, at operation 707, the processor 210 may detect the object (e.g., user). The processor 210 may detect the object using an IR sensor or a camera.

At operation 709, the processor 210 may extract features of the detected object, and at operation 711, the processor 210 may determine an ROI based on the extracted features. Here, the ROI may be a region in which the HR can be measured to correspond to the object. According to various embodiments, if the object corresponds to a user's face, the ROI may be a specific region (area) of the face (e.g., head temples, bags under eyes, or bag under a nose) in which the HR measurement is possible.

At operation 713, the processor 210 may determine whether the HR measurement is possible based on the determined ROI. That is, the processor 210 may determine whether the object is a living thing that is actually alive. Various embodiments of the present disclosure can prevent forgery that performs user authentication using only an iris image. If the HR measurement is impossible in the determined ROI, the processor 210 may determine that the user authentication has failed.

If the HR measurement is possible at operation 713, the processor 210, at operation 715, may complete the user authentication process. That is, if the HR measurement for the user is possible, the processor 210 may determine that the iris information that is recognized at operation 703 has not been forged.

Although not illustrated, the processor 210 may determine the HR based on the determined ROI, and may transfer information on the determined HR to a specific application.

Although not illustrated, if the user authentication is completed at operation 715, the processor 210 may store the ROI that is determined at operation 711 in a user DB (e.g., user DB 440 of FIG. 4). In the case of performing the HR measurement function in a state where the user authentication has been performed, the processor 210 may omit a process of determining the ROI, and may bring the ROI that corresponds to the authenticated user from the user DB.

According to various embodiments of the present disclosure, a method for determining a HR using an IR sensor may include receiving an image using the IR sensor, determining at least one ROI for measuring the HR in the received image, and determining the HR based on the at least one determined ROI.

According to various embodiments, the method may detect an object from the received image, extract features of the detected object, and determine the at least one ROI based on the extracted features of the object.

According to various embodiments, the method may extract locations of eyes, a nose, a mouth, and a forehead of a user as the features of the object if a user's face is included in the received image.

According to various embodiments, the method may further include recognizing an iris of a user using the IR sensor in response to a request for user authentication, determining whether measurement of the HR Is possible in the ROI, and completing the user authentication if the HR is measured.

According to various embodiments, the method may further include determining the HR of the user based on the determined ROI if the ROI is determined to correspond to the authenticated user.

According to various embodiments, the method may further include storing the at least one determined ROI in the memory to correspond to the authenticated user if the ROI is not determined to correspond to the authenticated user.

According to various embodiments, the method may measure a noise that occurs in the at least one ROI, and exclude the ROI from a candidate group of ROI in which measurement of the HR is possible if the measured noise exceeds a predetermined threshold value.

According to various embodiments, the method may determine the HR based on the candidate group of ROI in which the measurement of the HR is possible.

According to various embodiments, the method may receive data for measuring the HR from the at least one determined ROI, convert the received data into HR data, and determine the converted HR data as the HR.

According to various embodiments, the method may receive data that corresponds to an image change in the at least one determined ROI, and convert the received data into the HR to determine the HR.

According to various embodiments, the method may further include controlling the quantity of light of the IR sensor based on a use purpose of the IR sensor and a distance between an object and the IR sensor.

FIGS. 8A, 8B, 8C, and 8D are diagrams illustrating ROI that are determined to measure HRs according to various embodiments of the present disclosure.

Figure 8A:
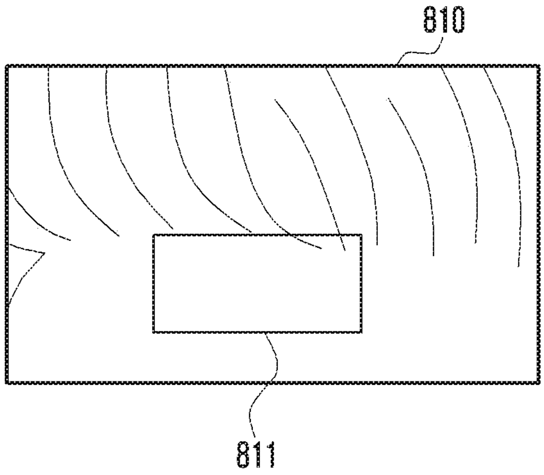
FIGS. 8A, 8B, 8C, and 8D are diagrams illustrating ROI that are determined to measure HRs according to various embodiments of the present disclosure.

Referring to FIG. 8A, a processor (processor 210 of FIG. 4) may extract features of an object (e.g., user's face), and may recognize a forehead 810 of a user based on the extracted features. Further, the processor 210 may search for a ROI 811 in which an image change occurs in the forehead 810 of the user. Further, the processor 210 may acquire one or more images that correspond to the ROI 811 that is a part of the forehead 810, and may measure a HR of the user based on the acquired images. In the case of performing user authentication, the processor 210 may store the ROI 811 in an ROI DB to correspond to the authenticated user.

According to various embodiments, in the case where the user performs user authentication, the electronic device may measure the HR in the ROI 811 that corresponds to the user without searching for the ROI 811 if the ROI 811 that corresponds to the user is stored in the ROI DB. The forehead 810 of the user may be hidden by hair, and the HR that is measured in the ROI 811 that is hidden by the hair may be the HR in which a lot of noise has occurred.

Figure 8B:
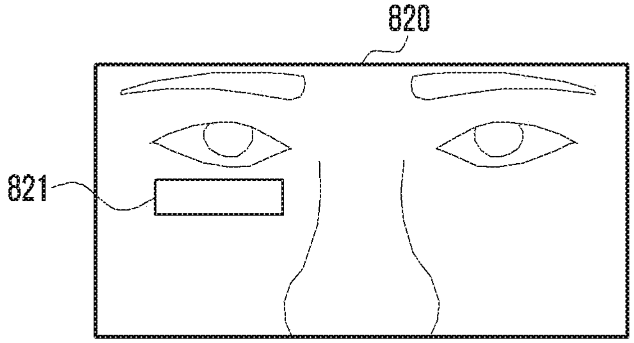

Referring to FIG. 8B, the processor 210 may extract the features of a face shape, and may recognize locations of the eyes and the nose 820 based on the extracted features. Further, the processor 210 may determine a bag 821 under the right eye of the user as the ROI. The processor 210 may acquire one or more images that correspond to the bag 821 under the right eye of the user, and may measure the HR of the user based on the acquired images. In the case of performing the user authentication, the processor 210 may store the bag 821 under the right eye of the user in the ROI DB as the ROI to correspond to the authenticated user.

Figure 8C:
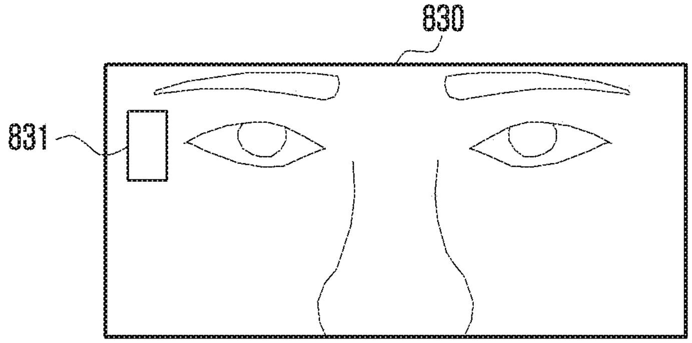

Referring to FIG. 8C, the processor 210 may extract the features of a face shape, and may recognize locations of the eyes 830 based on the extracted features. Further, the processor 210 may determine the right temple 831 of the user, in which an image change occurs, as the ROI. The processor 210 may acquire one or more images that correspond to the right temple 831 of the user, and may measure the HR of the user based on the acquired images. In the case of performing the user authentication, the processor 210 may store the right temple 831 of the user in the ROI DB as the ROI to correspond to the authenticated user.

Figure 8D:
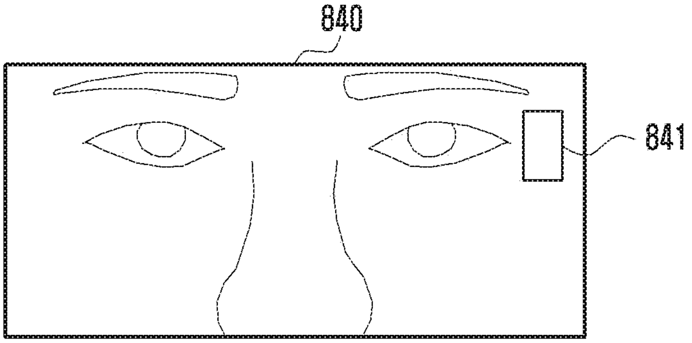

Referring to FIG. 8D, the processor 210 may extract the features of a face shape, and may recognize locations of the eyes 840 based on the extracted features. Further, the processor 210 may determine the left temple 841 of the user, in which an image change occurs, as the ROI. The processor 210 may acquire one or more images that correspond to the left temple 841 of the user, and may measure the HR of the user based on the acquired images. In the case of performing the user authentication, the processor 210 may store the left temple 841 of the user in the ROI DB as the ROI to correspond to the authenticated user.

FIGS. 9A, 9B, 9C, and 9D are diagrams illustrating experimental values that are obtained by measuring HRs in the ROI as illustrated in FIGS. 8A to 8D according to various embodiments of the present disclosure.

Figure 9A:
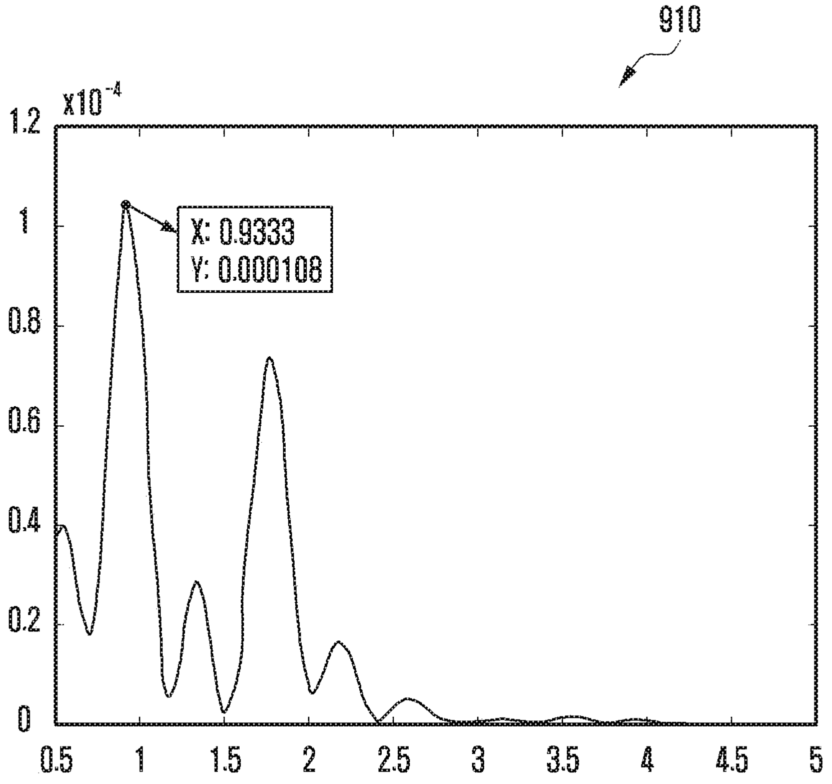
FIGS. 9A, 9B, 9C, and 9D are diagrams illustrating experimental values that are obtained by measuring HRs in the ROI as illustrated in FIGS. 8A to 8D according to various embodiments of the present disclosure.

FIG. 9A is a graph 910 illustrating experimental values of a HR measured in an ROI 811 that is a part of the forehead as illustrated in FIG. 8A. The graph 910 illustrates data that is measured for 3 seconds in the ROI 811 as illustrated in FIG. 8A. Referring to FIG. 9A, at the highest point of the graph that corresponds to the data, the X coordinate value may be 0.9333, and the Y coordinate value may be 0.000108. Since the X coordinate value at the highest point means the HR for one second, the HR that is measured based on the ROI 811 may be 55.98 bpm (0.9333*60=55.98).

Figure 9B:
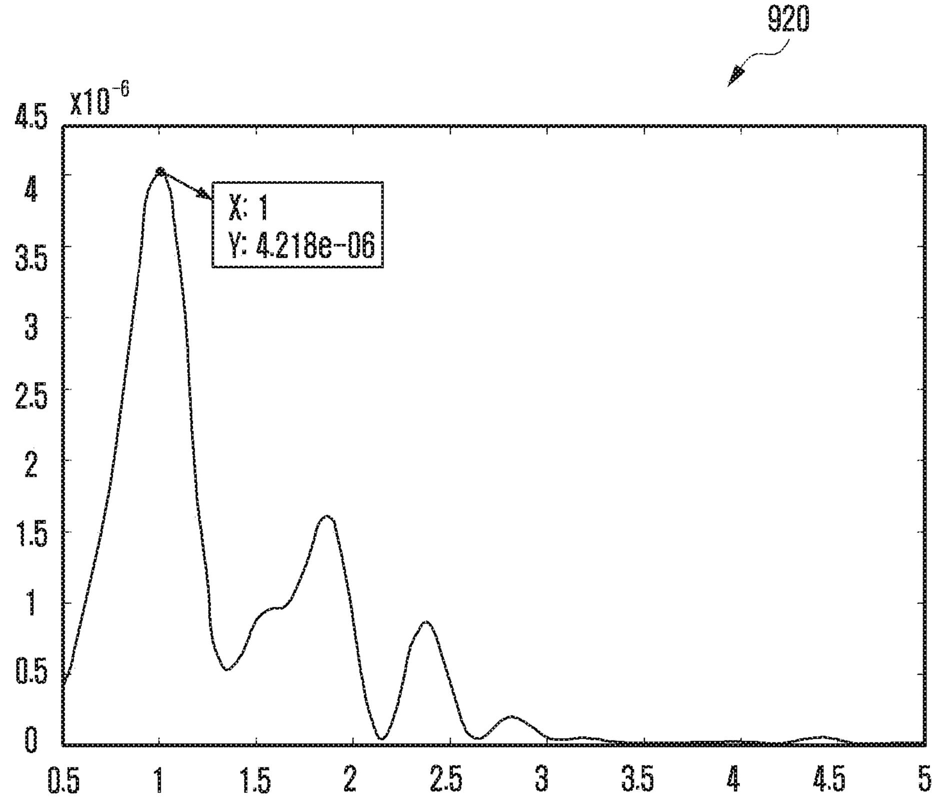

FIG. 9B is a graph 920 illustrating experimental values of a HR measured in a bag 821 under the right eye of the user as illustrated in FIG. 8B. The graph 920 illustrates data that is measured for 3 seconds in the bag 821 under the right eye as illustrated in FIG. 8B. Referring to FIG. 9B, at the highest point of the graph that corresponds to the data, the X coordinate value may be 1, and the Y coordinate value may be 4.218 e-06. Since the X coordinate value at the highest point means the HR for one second, the HR that is measured based on the bag 821 under the right eye may be 60.00 bpm (1*60=60).

Figure 9C:
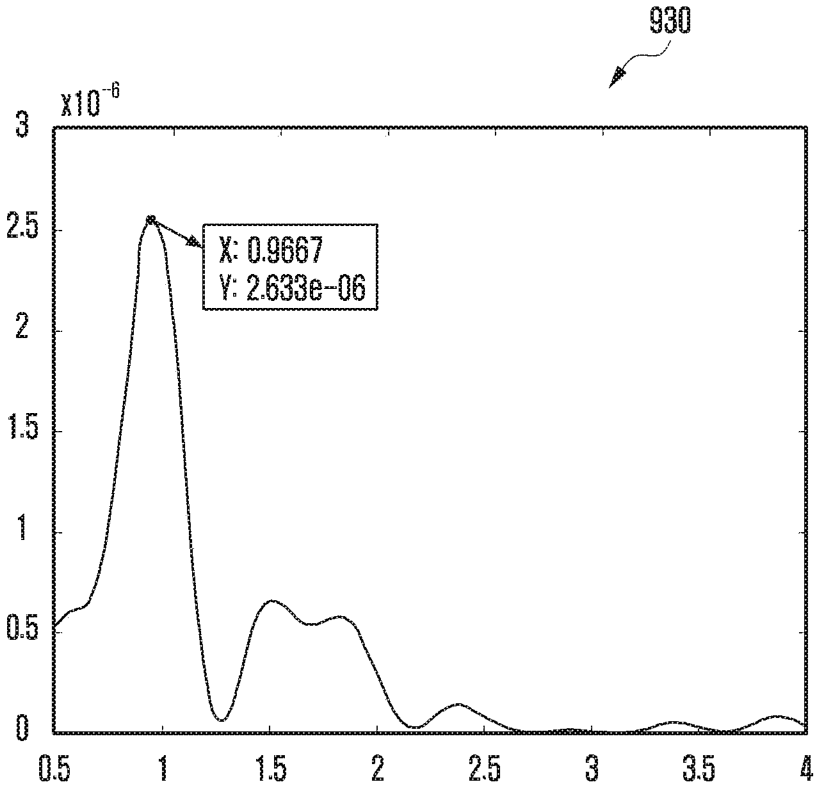

FIG. 9C is a graph 930 illustrating experimental values of a HR measured in the right temple 831 of the user as illustrated in FIG. 8C. The graph 930 illustrates data that is measured for 3 seconds in the right temple 831 of the user as illustrated in FIG. 8C. Referring to FIG. 9C, at the highest point of the graph that corresponds to the data, the X coordinate value may be 0.9667, and the Y coordinate value may be 2.633 e-06. Since the X coordinate value at the highest point means the HR for one second, the HR that is measured based on the right temple 831 may be 58.002 bpm (0.9667*60=58.002).

Figure 9D:
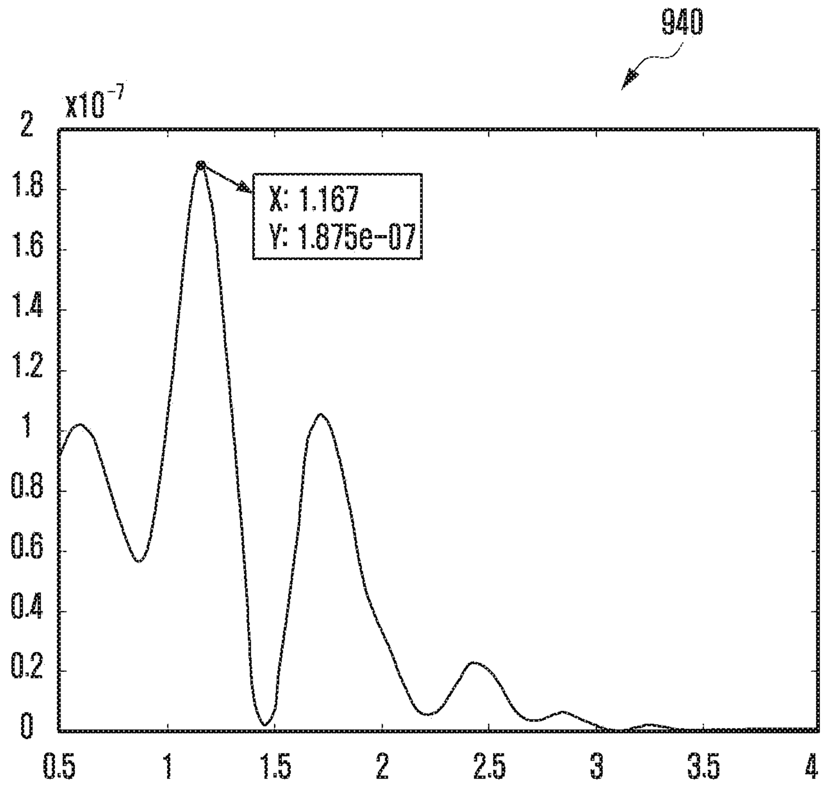

FIG. 9D is a graph 940 illustrating experimental values of a HR measured in the left temple 841 of the user as illustrated in FIG. 8D. The graph 940 illustrates data that is measured for 3 seconds in the left temple 841 of the user as illustrated in FIG. 8D. Referring to FIG. 9D, at the highest point of the graph that corresponds to the data, the X coordinate value may be 1.167, and the Y coordinate value may be 1.875 e-07. Since the X coordinate value at the highest point means the HR for one second, the HR that is measured based on the left temple 841 may be 70.02 bpm (1.167*60=70.02).

According to the various embodiments of the present disclosure, the electronic device may determine at least one ROI, and may measure the HR to correspond to the at least one ROI. According to various embodiments of the present disclosure, the electronic device may calculate the average value based on plural HRs that are measured in at least one ROI, and may expect the average value as the HR of the user.

Figure 10:
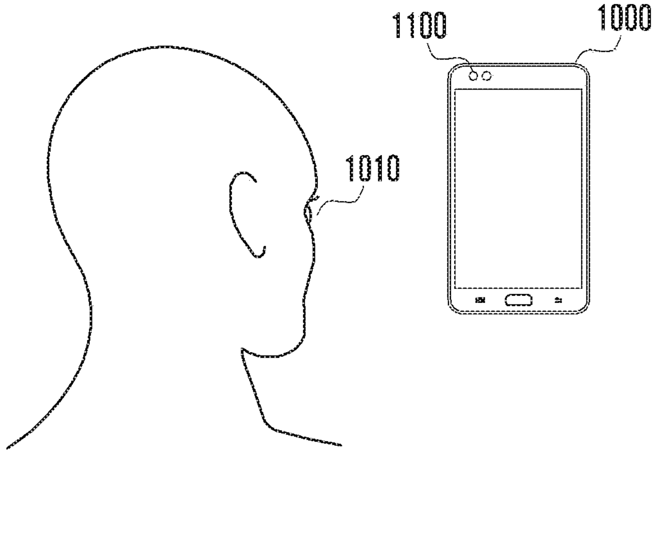
FIG. 10 is a diagram illustrating a process of measuring a HR of a user using an IR sensor according to an embodiment of the present disclosure.

FIG. 10 is a diagram illustrating a process of measuring an HR of a user using an IR sensor according to an embodiment of the present disclosure.

Referring to FIG. 10, various embodiments of the present disclosure may authenticate an iris 1010 of a user using a camera 1100 provided in an electronic device 1000. Here, the camera 1100 may include a camera module (camera module 291 of FIG. 2) and an IR sensor (IR sensor 240N of FIG. 2) that constitutes one light emitting unit. A processor of the electronic device 1000 may receive information on the iris 1010 of the user using the IR sensor that constitutes the light emitting unit of the camera 1100, and may perform authentication of the user.

At least part of the device (e.g., modules or functions thereof) or method (e.g., operations) according to various embodiments may be implemented as commands stored, e.g., in the form of program module, in a computer-readable storage medium. In case commands are executed by at least one processor, this processor may perform a particular function corresponding to the commands. The computer-readable storage medium may be, for example, the memory. At least some of the program module may be implemented (e.g., executed) by, for example, the processor. At least some of the program module may include, for example, a module, a program, a routine, a set of instructions, and/or a process for performing one or more functions.

The non-transitory computer-readable recording medium may include magnetic media such as a hard disk, a floppy disk, and a magnetic tape, optical media such as a compact disc read only memory (CD-ROM) and a DVD, magneto-optical media such as a floptical disk, and hardware devices specially configured to store and perform a program instruction. In addition, the program instructions may include high class language codes, which can be executed in a computer by using an interpreter, as well as machine codes made by a compiler. The aforementioned hardware device may be configured to operate as one or more software modules in order to perform the operation of various embodiments of this disclosure, and vice versa.

A module or programming module according to various embodiments may include or exclude at least one of the above-discussed elements or further include any other element. The operations performed by the module, programming module or any other element according to various embodiments may be executed sequentially, in parallel, repeatedly, or by a heuristic method. Additionally, some operations may be executed in different orders or omitted, or any other operation may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:

an infrared rays (IR) sensor;

a memory; and a processor electrically connected to the IR sensor and the memory, wherein the memory stores instructions which, when executed, cause the processor to:

receive an image using the IR sensor, recognize, in response to a request for user authentication, an iris of a user using the IR sensor, detect an object from the received image, extract features of the detected object, determine at least one region of interest (ROI) for measuring a heart rate (HR) based on the extracted features of the object, identify whether measurement of the HR is possible in the ROI, and complete the user authentication based on information of the iris if the measurement of the HR is possible even if the surroundings are darkened.

2. The electronic device of claim 1, wherein the instructions cause the processor to extract locations of eyes, a nose, a mouth, and a forehead of a user as the features if a user's face is included in the received image.

3. The electronic device of claim 1, wherein the instructions cause the processor to:

determine the HR of the user based on the determined ROI if the ROI is determined to correspond to the authenticated user, and store the at least one determined ROI in the memory to correspond to the authenticated user if the ROI is not determined to correspond to the authenticated user.

4. The electronic device of claim 1, wherein the instructions cause the processor to:

measure a noise that occurs in the at least one ROI, exclude the ROI from a candidate group of ROI in which measurement of the HR is possible if the measured noise exceeds a predetermined threshold value, and determine the HR based on the candidate group of ROI in which the measurement of the HR is possible.

5. The electronic device of claim 1, wherein the instructions cause the processor to:

receive data for measuring the HR from the at least one determined ROI, convert the received data into HR data, and determine the converted HR data as the HR.

6. The electronic device of claim 1, wherein the instructions cause the processor to:

receive data that corresponds to an image change in the at least one determined ROI, and convert the received data into the HR to determine the HR.

7. The electronic device of claim 1, wherein the instructions cause the processor to control a quantity of light of the IR sensor based on a use purpose of the IR sensor and a distance between an object and the IR sensor.

8. The electronic device of claim 1, wherein the IR sensor is composed of any one of a sensor that includes both a light emitting unit and a light receiving unit, a sensor built in a camera, or a sensor in which a sensor that is a light emitting unit and a camera that is a light receiving unit are associated with each other.

9. A method for determining a heart rate (HR) using an infrared rays (IR) sensor, the method comprising:

receiving an image using the IR sensor;

recognizing, in response to a request for user authentication, an iris of a user using the IR sensor;

detecting an object from the received image;

extracting features of the detected object;

determining at least one region of interest (ROI) for measuring the HR based on the extracted features of the object;

identifying whether measurement of the HR is possible in the ROI; and completing the user authentication based on information of the iris if the measurement of the HR is possible even if the surroundings are darkened.

10. The method of claim 9, wherein the extracting of the features of the object comprises extracting locations of eyes, a nose, a mouth, and a forehead of a user as the features if a user's face is included in the received image.

11. The method of claim 9, further comprising:

determining the HR of the user based on the determined ROI if the ROI is determined to correspond to the authenticated user; and storing the at least one determined ROI in a memory to correspond to the authenticated user if the ROI is not determined to correspond to the authenticated user.

12. The method of claim 9, wherein the determining of the HR comprises:

measuring a noise that occurs in the at least one ROI;

excluding the ROI from a candidate group of ROI in which measurement of the HR is possible if the measured noise exceeds a predetermined threshold value; and determining the HR based on the candidate group of ROI in which the measurement of the HR is possible.

13. The method of claim 9, wherein the determining of the HR comprises:

receiving data for measuring the HR from the at least one determined ROI;

converting the received data into HR data; and determining the converted HR data as the HR.

14. The method of claim 9, wherein the determining of the HR comprises:

receiving data that corresponds to an image change in the at least one determined ROI; and converting the received data into the HR to determine the HR.

15. The method of claim 9, further comprising controlling a quantity of light of the IR sensor based on a use purpose of the IR sensor and a distance between an object and the IR sensor.

* * * * *